US012205706B2

(12) United States Patent
Zhao et al.

(10) Patent No.: US 12,205,706 B2
(45) Date of Patent: Jan. 21, 2025

(54) METHOD AND SYSTEM FOR COMPUTER AIDED DETECTION OF ABNORMALITIES IN IMAGE DATA

(71) Applicant: Siemens Healthcare GmbH, Erlangen (DE)

(72) Inventors: Yiyuan Zhao, Malvern, PA (US); Siqi Liu, Princeton, NJ (US); Anna Jerebko, Paoli, PA (US); Parmeet Bhatia, Paoli, PA (US); Gerardo Hermosillo Valadez, West Chester, PA (US)

(73) Assignee: SIEMENS HEALTHINEERS AG, Forchheim (DE)

( * ) Notice: Subject to any disclaimer, the term of this patent is extended or adjusted under 35 U.S.C. 154(b) by 426 days.

(21) Appl. No.: 17/209,460

(22) Filed: Mar. 23, 2021

(65) Prior Publication Data
US 2021/0319879 A1 Oct. 14, 2021

(30) Foreign Application Priority Data

Apr. 8, 2020 (EP) .................... 20168789

(51) Int. Cl.
*G16H 30/40* (2018.01)
*G06N 3/08* (2023.01)
(Continued)

(52) U.S. Cl.
CPC ............. *G16H 30/40* (2018.01); *G06N 3/08* (2013.01); *G06T 3/02* (2024.01); *G06T 5/70* (2024.01);
(Continued)

(58) Field of Classification Search
CPC ......... G16H 30/40; G06T 3/00; G06T 3/0006; G06T 5/002; G06T 5/003; G06T 7/0012;
(Continued)

(56) References Cited

U.S. PATENT DOCUMENTS 8,879,813 B1 * 11/2014 Solanki .................... G06T 3/14
382/128
10,499,857 B1 * 12/2019 Nguyen ................. G06N 3/045
(Continued)

FOREIGN PATENT DOCUMENTS

WO    WO 2019245597 A1    12/2019

OTHER PUBLICATIONS

Calvo-Zaragoza, Jorge et al: "Ensemble classification from deep predictions with test data augmentation", Soft Computing, Springer Verlag, vol. 24, No. 2, pp. 1423-1433, XP036980930, ISSN: 1432-7643, DOI: 10.1007/S00500-019-03976-7; 2019.
(Continued)

*Primary Examiner* — Edward F Urban
*Assistant Examiner* — Jongbong Nah
(74) *Attorney, Agent, or Firm* — Harness, Dickey & Pierce, P.L.C.

(57) ABSTRACT

A computer-implemented method is for classifying a region of interest in a medical image data set depicting a body part of a patient. The region of interest contains an object of potential pathological relevance. In an embodiment, the method includes a plurality of steps. One step is directed to generate a plurality of different representations of the region of interest. Another step is directed to determine, for each of the representations, a classification to generate a corresponding plurality of classifications. Thereby, each classification indicates a pathological relevance of the object in the respective representation. Yet, a further step is directed to calculate an ensemble classification for the region of interest based on the plurality of classifications.

15 Claims, 5 Drawing Sheets

(51) Int. Cl.
*G06T 3/00* (2024.01)
*G06T 3/02* (2024.01)
*G06T 5/00* (2024.01)
*G06T 5/70* (2024.01)
*G06T 5/73* (2024.01)
*G06T 7/00* (2017.01)

(52) U.S. Cl.
CPC .............. *G06T 5/73* (2024.01); *G06T 7/0012* (2013.01); *G06T 2207/20081* (2013.01); *G06T 2207/20104* (2013.01)

(58) Field of Classification Search
CPC . G06T 2207/10072; G06T 2207/20081; G06T 2207/20084; G06T 2207/20104
See application file for complete search history.

(56) References Cited

U.S. PATENT DOCUMENTS

| | | | |
|---|---|---|---|
| 2009/0067693 A1 | 3/2009 | Shinagawa et al. | |
| 2009/0092300 A1 | 4/2009 | Jerebko et al. | |
| 2016/0321427 A1 | 11/2016 | Bogoni et al. | |
| 2018/0368781 A1* | 12/2018 | De Man | A61B 5/055 |
| 2019/0303760 A1* | 10/2019 | Kumar | G06V 10/82 |
| 2020/0065940 A1* | 2/2020 | Tang | G06T 3/40 |
| 2020/0085382 A1* | 3/2020 | Taerum | G06T 7/0016 |
| 2021/0090257 A1* | 3/2021 | Bhatia | G06T 7/11 |
| 2021/0225511 A1* | 7/2021 | Kiraly | G06F 18/213 |

OTHER PUBLICATIONS

Li, Xuechen et al:, "Multi-resolution convolutional networks for chest X-ray radiograph based lung module detection", Artificial Intelligence in Medicine, Els Ev l b b ER, N L, vol. 103, Oct. 28, 2019 (Oct. 28, 2019), XP086078294, ISSN: 0933-3657, DOI: 10.1016/J.ARTMED.2019.101744; 2019.

Qinghe, Zheng et al: "A Full Stage Data Augmentation Method in Deep Convolutional Neural Network for Natural Image Classification", Discrete Dynamics in Nature and Society, vol. 2020, pp. 1-11, XP055716316, ISSN: 1026-0226, DOI: 10.1155/2020/4706576; 2020.

Gonzalez-Diaz, Ivan: "DermaKNet : Incorporating the Knowledge of Dermatologists to Convolutional Neural Networks for Skin Lesion Diagnosis", IEEE Journal of Biomedical and Health Informatics, vol. 23, No. 2, pp. 547-559, XP011713048, ISSN: 2168-2194, DOI: 10.1109/JBHI.2018.2806962; 2019.

Extended European Search Report dated Aug. 6, 2020.

Perez, Fabio et al.; "Data Augmentation for Skin Lesion Analysis", arxiv.org, Cornell University Library, 201 Olin Library Cornell University Ithaca, NY 14853; published: Sep. 5, 2018; XP081079213; DOI: 10.1007/978-3-030-01201-4_33.

* cited by examiner

METHOD AND SYSTEM FOR COMPUTER AIDED DETECTION OF ABNORMALITIES IN IMAGE DATA

PRIORITY STATEMENT

The present application hereby claims priority under 35 U.S.C. § 119 to European patent application number EP 20168789.4 filed Apr. 8, 2020, the entire contents of which are hereby incorporated herein by reference.

FIELD

Example embodiments of the invention generally relate to methods and systems for improved data mining and false positive reduction in computer-aided detection (CADe), computer-aided diagnosis (CADx) and artificial intelligent agents.

BACKGROUND

Advances in medical imaging, e.g., employing computed tomography or magnetic resonance systems, allow for reproducing tiniest changes in the anatomy of a patient. As a result of the increased performance of these systems, there is increased focus on the early detection of diseases with improved chances of success of the following treatment. However, for radiologists, this increased focus also has negative aspects. The procedure of visually analyzing radiology images is often challenging. For instance, the density and tissue type of organs are highly varied and in turn present a high variety of visual features. Additionally, background visual patterns can obscure the early signs of malignancies which may then be easily overlooked by the human eye.

Therefore, the manual classification of the spatial distribution of abnormalities or patterns inevitably leads to errors owing to mistakes, human error, and/or details too fine for the human eye to detect. Thus, the analysis of medical images may lead to false negatives which may cause missed treatment. Likewise, the evaluation may prompt false positives which may cause unwanted psychological and suboptimal downstream diagnostic and treatment consequences. What is more, the reliable detection of abnormalities and/or features in medical images often requires highly experienced physicians further increasing their workload. Moreover, the human component in evaluating image data adds a degree of subjectivity which is often unwanted.

To cope with such problems, computer-aided detection (CADe) and computer-aided diagnosis (CADx) systems are being developed. Hereafter both types of systems will be referred to as CAD systems. CAD systems are technologies to help radiologists interpret medical images. A common use of CAD systems is to automatically identify suspicious regions in a medical image. Such suspicious regions may contain image patterns indicative of abnormalities which may comprise cancerous growths, masses, abscesses, lacerations, calcifications, lesions and/or other irregularities within biological tissue and which can cause serious medical problems if left undetected.

Basically, an ideal CAD system should be able to securely identify all actual abnormalities without generating any false positives. This may sound straightforward but is very difficult to achieve in practice as this means fulfilling two conflicting requirements. At the one hand, CAD systems have to be highly sensible so that no potentially relevant objects remain undetected. On the other hand, a highly sensitive detection inevitably increases the likelihood of generating false positives.

SUMMARY

At least one embodiment of the present invention is directed to addressing the above conflict and provide a method and/or a corresponding system capable of securely identifying and/or detecting objects of pathological relevance in medical image data. In particular, at least one embodiment of the present invention provides an improved computer-implemented method for classifying objects and/or associated regions of interest in medical image data so as to support a user/physician/radiologist/pathologist in deriving a medical diagnosis from a medical image volume.

Embodiments are directed to methods for classifying a region of interest in a medical image data set, for detecting pathologically relevant abnormalities in a medical image data set, corresponding systems, a corresponding method for training a trained function, a corresponding computer-program product and computer-readable storage medium. Alternative and/or preferred embodiments are subject of the claims.

According to an embodiment, a computer-implemented method for classifying a region of interest in a medical image data set depicting a body part of a patient is provided, wherein the region of interest contains an object of potential pathological relevance. The method comprises a step of generating a plurality of different representations of the region of interest. Another step is directed to determine, for each of the representations, a classification to generate a corresponding plurality of classifications, wherein each classification indicates a pathological relevance of the object in the respective representation. Yet, a further step is directed to calculate an ensemble classification for the region of interest based on the plurality of classifications.

That being the, according to another embodiment of the invention, a computer-implemented method is provided for detecting pathologically relevant abnormalities in a medical image data set depicting a body part of a patient. The method comprises a plurality of steps. One step is directed to receiving a medical image data set. A further step is directed to determine a set of candidate abnormalities in the medical image data set. Subsequently, the following steps are performed for each of the candidate abnormalities comprised in the set of candidate abnormalities: generating a plurality of different representations of the respective candidate abnormality, determining a corresponding plurality of classifications, wherein each of the classifications corresponds to one of the plurality of representations, and determining an ensemble classification of the respective candidate abnormality based on the plurality of classifications. Finally, a detection result is generated using the ensemble classifications respectively generated for each of the candidate abnormalities.

According to another embodiment, the inventive idea may also be employed for general image processing outside of the medical context. For such applications as well, the proposed data augmentation by generating multiple representations of an object to be classified helps to reduce systematic errors and improves the accessibility of image features for classification. Accordingly, the classification result is more accurate and reliable. In the light of this, according the aspect, a method for classifying a region of interest in an image data set is provided, which method comprises a plurality of steps. One step is directed to generating a plurality of different representations of the region of interest. Another step is directed to determine, for each of the representations, a classification to generate a corresponding plurality of classifications. Another step is directed to calculate an ensemble classification for the region of interest based on the plurality of classifications.

Moreover, according to another embodiment, the data augmentation may also be used during training a trained function for classifying objects in computer aided diagnosis of medical image data sets depicting a body part of a patient. Such method includes the steps of: providing a training data set, wherein the training data set includes: training image data relating to an image volume containing an object to be classified; and a target classification of the object; generating N>1 different representations of the object, each of the N different representations comprising processed image data generated by applying one or more image processing steps to the training image data, generating a classification of the object by applying the trained function to one of the representation, comparing the classification with the target classification, and adjusting the trained function as a function of the comparison.

According to an embodiment, a system for detecting pathologically relevant abnormalities in a medical image data set depicting a body part of a patient is provided. The system comprises an interface unit for receiving a medical image data set. Further the system comprises a computing unit configured to determine a set of candidate abnormalities in the medical image data set. The computing unit is further configured to generate, for each of the candidate abnormalities comprised in the set of candidate abnormalities, a plurality of different representations of the respective candidate abnormality. The computing unit is further configured to determine, for each of the candidate abnormalities comprised in the set of candidate abnormalities, a corresponding plurality of classifications, wherein each of the classifications corresponds to one of the plurality of representations. Further, the computing unit is configured to determine, for each of the candidate abnormalities comprised in the set of candidate abnormalities, an ensemble classification of the respective candidate abnormality based on the plurality of classifications. Finally, the computing unit is configured to generate a detection result using the ensemble classifications.

The computing unit may be realized as a data processing system or as a part of a data processing system. Such a data processing system can, for example, comprise a cloud-computing system, a computer network, a computer, a tablet computer, a smartphone and/or the like. The computing unit can comprise hardware and/or software. The hardware can comprise, for example, one or more processors, one or more memories and combinations thereof. The one or more memories may store instructions for carrying out the method steps according to an embodiment of the invention. The hardware can be configurable by the software and/or be operable by the software. Generally, all units, sub-units or modules may at least temporarily be in data exchange with each other, e.g., via a network connection or respective interfaces. Consequently, individual units may be located apart from each other.

The interface unit may comprise an interface for data exchange with a local server or a central web server via internet connection for receiving the reference image data or follow-up image data. The interface unit may be further adapted to interface with one or more users of the system, e.g., by displaying the result of the processing by the computing unit to the user (e.g., in a graphical user interface) or by allowing the user to adjust parameters for image processing and/or to select the candidate abnormalities.

According to another embodiment, the invention further relates to an image analysis system comprising the system for detecting pathologically relevant abnormalities in a medical image data set and a medical image system configured to acquire, store and/or forward follow-up medical images (comprising the reference image data and the follow-up image data). Thereby, the interface unit is configured to receive the medical image data set from the medical image system.

According to an embodiment, the medical image system comprises one or more archive stations for storing medical image data sets, which may be realized as a cloud storage or as a local or spread storage, e.g., as a PACS (Picture Archiving and Communication System). Further, the medical image system may comprise one or more medical imaging modalities, such as a computed tomography system, a magnetic resonance system, an angiography (or C-arm X-ray) system, a positron-emission tomography system, a mammography system, system for acquiring digital pathology images or the like.

According to another embodiment, the present invention is directed to a computer program product comprising program elements which induce a computing unit of a system for detecting pathologically relevant abnormalities in a medical image data set to perform the steps according to an embodiment of the above method, when the program elements are loaded into a memory of the computing unit.

According to another embodiment, the present invention is directed to a computer-readable medium on which program elements are stored that are readable and executable by a computing unit of a system detecting pathologically relevant abnormalities in a medical image data set, in order to perform steps of an embodiment of the inventive method, when the program elements are executed by the computing unit.

The realization of an embodiment of the invention by a computer program product and/or a computer-readable medium has the advantage that already existing providing systems can be easily adopted by software updates in order to work as proposed by an embodiment of the invention.

The computer program product can be, for example, a computer program or comprise another element next to the computer program as such. This other element can be hardware, e.g., a memory device, on which the computer program is stored, a hardware key for using the computer program and the like, and/or software, e.g., a documentation or a software key for using the computer program. The computer program product may further comprise development material, a runtime system and/or databases or libraries. The computer program product may be distributed among several computer instances.

According to another embodiment, the present invention is directed to a computer-implemented method for classifying a region of interest in a medical image data set depicting a body part of a patient, the region of interest including an object of potential pathological relevance, the computer-implemented method comprising:
  generating a plurality of different representations of the region of interest;
  determining a respective classification for each respective representation, of the different representations, to generate a corresponding plurality of classifications, each respective classification indicating a pathological relevance of the object in a corresponding respective representation, the respective classifications forming a plurality of respective classifications; and calculating an ensemble classification for the region of interest based on the plurality of respective classifications.

According to another embodiment, the present invention is directed to a computer-implemented method for detecting pathologically relevant abnormalities in a medical image data set depicting a body part of a patient, the computer-implemented method comprising:

receiving a medical image data set;

determining a set of candidate abnormalities in the medical image data set;

for each respective candidate abnormality included in the set of candidate abnormalities:

generating a plurality of different representations of the respective candidate abnormality, determining a corresponding plurality of classifications, each respective classification of the plurality of classifications, corresponding to one of the plurality of representations, and each of the respective classifications being indicative of pathological relevance of the respective candidate abnormality in the corresponding one of the plurality of representations, and determining an ensemble classification of the respective candidate abnormality based on the plurality of classifications; and generating a detection result using the ensemble classifications of each of the respective candidate abnormalities.

According to another embodiment, the present invention is directed to a system for detecting pathologically relevant abnormalities in a medical image data set depicting a body part of a patient, the system comprising:

an interface unit configured to receive a medical image data set; and a processor configured to:

determine a set of candidate abnormalities in the medical image data set;

for each respective candidate abnormality included in the set of candidate abnormalities:

generate a plurality of different representations of the respective candidate abnormality;

determine a corresponding plurality of classifications, each respective classification of the plurality of classifications, corresponding to one of the plurality of representations;

determine an ensemble classification of the respective candidate abnormality based on the plurality of classifications;

generate a detection result using the ensemble classifications of each of the respective candidate abnormalities.

According to another embodiment, the present invention is directed to a non-transitory computer program product storing program elements, which induce a computing unit of a system to perform the method of an embodiment, when the program elements are loaded into a memory of the computing unit and executed.

According to another embodiment, the present invention is directed to a non-transitory computer-readable medium storing program elements, readable and executable by a computing unit of a system to perform the method of an embodiment, when the program elements are executed by the computing unit.

BRIEF DESCRIPTION OF THE DRAWINGS

Characteristics, features and advantages of the above de-scribed invention, as well as the manner they are achieved, become clearer and more understandable in the light of the following description and embodiments, which will be described in detail with respect to the figures. This following description does not limit the invention on the contained embodiments. Same components or parts can be labeled with the same reference signs in different figures. In general, the figures are not drawn to scale. In the following.

DETAILED DESCRIPTION OF THE EXAMPLE EMBODIMENTS

Figure 1:
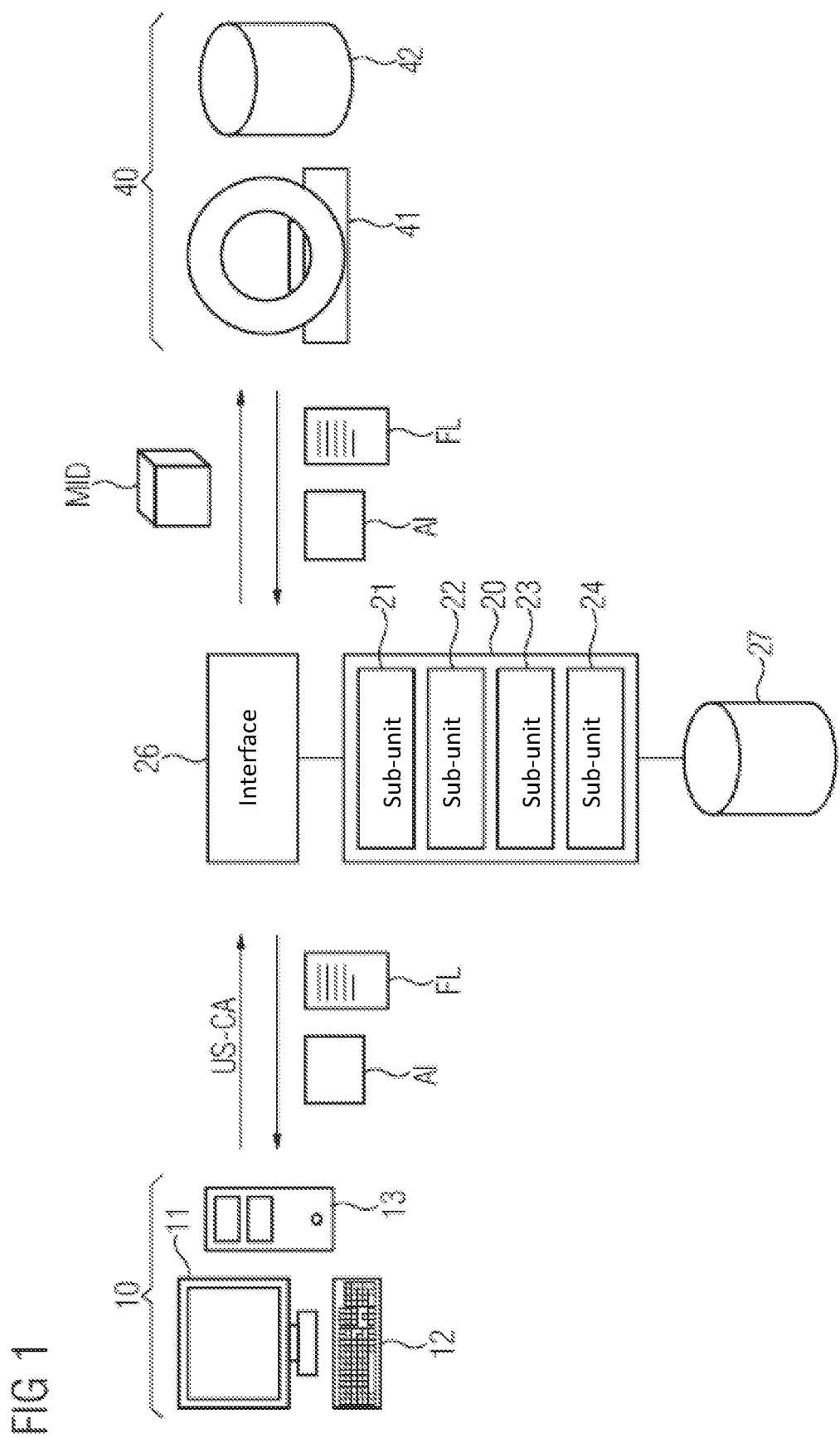
FIG. 1 depicts a system for classifying one or more objects in a medical image data set according to an embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In the following, embodiments according to the present invention are described with respect to the apparatuses as well as with respect to the methods. Features, advantages or alternative embodiments described herein can likewise be assigned to other objects and vice versa. In other words, claims and embodiments addressing the inventive method can be improved by features described or claimed with respect to the apparatuses. In this case, e.g., functional features of the method are embodied by objective units or elements of the apparatus.

According to an embodiment, a computer-implemented method for classifying a region of interest in a medical image data set depicting a body part of a patient is provided, wherein the region of interest contains an object of potential pathological relevance. The method comprises a step of generating a plurality of different representations of the region of interest. Another step is directed to determine, for each of the representations, a classification to generate a corresponding plurality of classifications, wherein each classification indicates a pathological relevance of the object in the respective representation. Yet, a further step is directed to calculate an ensemble classification for the region of interest based on the plurality of classifications.

The medical image data set may relate to two-dimensional image data providing two dimensions in space. Further, the medical image data set may relate to three-dimensional image data providing three dimensions in space. The medical image data set depicts a body part of a patient in the sense that it contains two- or three-dimensional image data of the patient's body part. The medical image data may, for example, be in the form of an array of pixels or voxels. Such arrays of pixels or voxels may be representative of intensity, absorption or other parameter as a function of three-dimensional position, and may, for example, be obtained by suitable processing of measurement signals obtained by a medical imaging modality. A medical imaging modality corresponds to a system used to generate or produce medical images. For example, a medical imaging modality may be a computed tomography system (CT system), a magnetic resonance system (MR system), an angiography (or C-arm X-ray) system, a positron-emission tomography system (PET system) or the like. The depicted body part of the patient in general will comprise a plurality of anatomies and/or organs. Taking a chest image as an example, the medical image data may show lung tissue, the rib cage, lymph nodes and others.

Dependent on the medical image data set, the region of interest may likewise be two- or three-dimensional and contain two- or three-dimensional image data. A region of interest may be understood as a group of image elements like pixels or voxels. The region of interest comprises at least one image element of the medical image data set. The region of interest represents an area or a volume within the depicted body part of the patient, which is of specific interest for the radiologist analyzing the current examination image of the patient. For example, the region of interest is positioned such that it comprises or covers a suspicious or atypical or abnormal anatomical structure or object like a lesion or a calcification or the like. Preferably, the region of interest covers additional neighboring tissue representing unsuspicious areas for providing additional contextual information. The region of interest may have an arbitrary shape, preferably the region of interest is of circular or quadratic form. The region of interest may relate to an image area or volume which has been identified as suspicious. Accordingly, it may contain an object of potential pathological relevance (a candidate abnormality). The object of potential pathological relevance may relate to an image pattern encoded in the image data comprised in the region of interest. The term "potential pathological relevance" may mean that the object may relate to an abnormality in the body part requiring the further attention of the user, such as a cancerous growth, nodule, mass, abscess, laceration, calcification, lesion and/or other irregularity in human tissue.

The region of interest thus may generally comprise the object and some space around the object. Dimensions and shape of the region of interest are usually not fixed but may vary according to the object contained and/or the way the object has been identified in the first place. In some implementations, the region of interest may comprise the entire field of view of the medical image data set. According to other implementations, the region of interest may result from cropping a patch/volume form the medical image data set at the location of the object. The region of interest containing the object (the candidate abnormality) may be considered as offering a view or representation of the object. In other words, the object is depicted by the image data comprised in the region of interest. Further analysis of this representation may provide an estimate about whether or not the object relates to an actual abnormality or to a false positive.

In order to increase the basis for this decision, the number of views/representations of the object is augmented by generating a plurality of representations of the region of interest. Self-speaking, one of the plurality of representations may be the original representation of the object itself, e.g., in the form of the region of interest. Being, generated/derived from the medical image data set, the representations may be two- or three-dimensional medical images themselves, providing two or three dimensions in space. The plurality of representations may be chosen such that they provide different views of the region of interest and the object therein comprised. These different views may comprise different viewing angles, different resolutions, different image sections, different scaling levels, different homogeneous and inhomogeneous deformations, the exertion of different imaging filters and so forth. Thus, the representations may be seen as comprising processed image data generated from original image data comprised in the medical image data set. Thus, generating a plurality of different representations for one region of interest may be seen as a data augmentation step.

This augmentation step enables to not only derive one classification for an object/a region of interest but a corresponding plurality of classifications—i.e., one classification for each representation. A classification generally may be conceived as a statement as to the pathological relevance of an object/the region of interest in view of the respective representation. "Pathological relevance" may be interpreted as a measure whether or not the region of interest requires further investigation (either by the user or by some other computer implemented method). Indicating the pathological relevance may mean indicating whether the object is pathological relevant or not. Further, indicating the pathological relevance may mean indicating whether the object is an actual (pathological) abnormality in the body part of the patient. Still further, indicating the pathological relevance may mean indicating whether the object relates to a false positive (i.e., not relating to an actual abnormality). The classification may relate to the object comprised in the region of interest but may likewise be conceived as a classification of the region of interest as such. The classification may be binary (e.g., relevant vs. not relevant; actual abnormality vs. false positive). Further, the classification may be in the form a confidence score for the presence of an actual abnormality. Further, the classification may comprise additional diagnostic information such as a degree of malignancy, calcification, fat deposition, solidification and so forth. The step of determining a classification may comprise providing a classifier (or classifying function) and inputting the plurality of representations into the classifier (either sequentially or at once). The classifier then is configured to generate an output in the form of a classification for each of the representations. Specifically, the classifier may be configured to input image data (either original or processed) and output a classification of an object comprised in the input image data (the object being comprised, e.g., in the form of an image pattern). At the end of the classification step stands a classification for each of the representations. If N representations are generated, N classifications result. Each of the classifications provides an indication of the pathological relevance of the object/the region of interest in the view provided by the corresponding representation.

In a subsequent step, the plurality of classifications is used to calculate an ensemble classification of the object/the region of interest. The ensemble classification may generally be of the same form as the individual classifications generated on the basis of the individual representations. In particular, the ensemble classification may likewise provide a statement regarding the pathological relevance of the object/ the region of interest. Just like the individual classifications, the ensemble classification may provide a binary result, a confidence score, and/or additional diagnostic information.

Since the ensemble classification is based on the individual classifications of the individual classification, all representations may be factored in for deciding about the nature of the region of interest/the object contained in the region of interest. This not only augments the basis for the decision but helps to filter out any bias stemming from the view provided by the original region of interest. For instance, the generation of different representations enables to review the region of interest from different viewing angles during classification. This makes it possible to extract more features from the different views as compared to merely relying on one representation. Hence, the final decision made by considering multiple features of the region of interest becomes more robust. Therefore, candidate abnormalities can be more accurately classified which in turn considerably decreases the number of false positives. By consequence, the user is provided with more accurate and reliable detection results. All this considerably improves the support for a user when confronted with the task of deriving a medical diagnosis from medical image data. Moreover, the above method steps make it possible to increase the sensitivity in an upstream detection stage of candidate abnormalities without deteriorating the overall detection accuracy.

That being the, according to another embodiment of the invention, a computer-implemented method is provided for detecting pathologically relevant abnormalities in a medical image data set depicting a body part of a patient. The method comprises a plurality of steps. One step is directed to receiving a medical image data set. A further step is directed to determine a set of candidate abnormalities in the medical image data set. Subsequently, the following steps are performed for each of the candidate abnormalities comprised in the set of candidate abnormalities: generating a plurality of different representations of the respective candidate abnormality, determining a corresponding plurality of classifications, wherein each of the classifications corresponds to one of the plurality of representations, and determining an ensemble classification of the respective candidate abnormality based on the plurality of classifications. Finally, a detection result is generated using the ensemble classifications respectively generated for each of the candidate abnormalities.

"Receiving" in the framework of the application may mean that the medical image data set is acquired from the medical imaging modalities. Further "receiving" may mean that it is acquired from an appropriate memory such as a picture archiving and communication system (PACS) or any other suitable medical image storing facility. Further "receiving" may mean that the medical image data is received for further processing on a request base by a further computer-implemented algorithm.

The step of determining a set of candidate abnormalities may be performed manually by the user, automatically by some suited detection algorithm, or semi-automatically. "Manually" may mean that the user interactively indicates one or more candidate abnormalities in the medical image data set (e.g., by clicking on a suspicious image pattern). "Automatically" may mean that the medical image data set is input into a designated algorithm or function (subsequently also designated as candidate generation function) which is configured to analyze a medical image data set for candidate abnormalities. "Semi-automatically" may involve retrieving a set of candidate abnormalities for selection by a user. The set of candidate abnormalities can comprise any number of candidate abnormalities, including zero abnormalities (if the medical image data set does not comprise any) or one abnormality. Determining a candidate abnormality may comprise providing its coordinates (e.g., in the form of the center coordinates of the candidate abnormality) and/or an indication of the size of the candidate abnormality. Further, determining a candidate abnormality may comprise providing a region of interest comprising the candidate abnormality.

The above detection method may be seen as being divided into two stages: a detection stage where a number of candidate abnormalities is detected, and a filtering stage in which candidate abnormalities are classified. The filtering stage may employ a classifier provided with representations generated by transforming/processing the original image data containing the candidate abnormality in multiple different ways and, optionally, appropriately cropping a patch/volume at the location of each candidate abnormality. The classifier may then classify, for each representation, whether or not the candidate abnormality relates to an actual abnormality or to a false positive and provide a corresponding classification. In other words, the filter stage is based on the evaluation of a plurality of representations of each candidate abnormality, each representation comprising processed image data of the candidate abnormality and some surrounding tissue.

The data augmentation in the filtering stage (i.e., the generation of a plurality of different representations) optimally complements the detection stage as candidate abnormalities can be more securely classified according to pathological relevance. This has the benefit that the sensitivity in the detection stage can be increased without adversely affecting the accuracy of the overall method.

The number of representations is not particularly limited. For instance, one representation may be provided for by the region of interest itself. Already one additional representation provides an additional view on the matter and may improve the classification result. (That being the, it is pointed out that already generating one additional representation alongside the original representation in the form of the field of view falls under the step of generating a plurality of representations—since a plurality of representations results.) However, providing more than just two representations will further improve the classification result. For instance, any number between 2 and 48 may be used. Specifically, the inventors determined that using 4 to 24 and, in particular, 8 to 16 representations provides a good compromise between improved classification results and computational costs.

According to an embodiment, in the step of generating, the plurality of different representations is generated by using one or more different image processing steps, preferably, by applying one or more different image processing steps to image data associated with the region of interest.

The image data associated with the region of interest may at least comprise the image data of the object to be classified. Additionally, the image data associated with the region of interest may comprise image data pertaining to some area surrounding the object. It may comprise all or part of the pixels/voxel of the region of interest. Further, the image data associated with the region of interest may also extend beyond the actual region of interest, for instance, if a wider field of view is required for a particular image processing step.

Relying on image processing steps has the benefit that the representations can be generated rather easily and swiftly. Moreover, it is possible to rely on a plethora of established image processing tools ranging from image cropping over geometric transformations to the application of all kinds of image filters. In general, an image processing step will transform original image data contained in the medical image data set into processed image data. Image processing may also relate to the identical transformation where the image data as such remains unchanged (apart from applying an appropriate cropping, for instance). The image processing may be applied to all of the image data comprised in the medical image data set or to only part of the image data, e.g., the image data in the vicinity of the object, which vicinity may be identical or different from the region of interest. Importantly, different image processing steps may be combined for generating a representation.

According to an embodiment, the image processing steps include one or more mathematical transformations of image data in the region of interest, the mathematical transformations, in particular, including affine and/or non-affine transformations.

Using mathematical transformations efficiently increases the number of "views" of an object or region of interest, which makes it possible to extract an overall greater number of features from the image data and use it for classification. The mathematical transformations may be applied to precisely the image data contained in the region of interest. Alternatively, also image data outside of the actual region of interest may be included and subjected to the mathematical transformations as this may prevent boundary effects. Vice versa, the mathematical transformations may be limited to (sub-)portions of the region of interest. Prior or after the transformation(s), the image data may be appropriately cropped so as to generate image patches/volumes suited for further processing. Affine transformations are defined as automorphism of an affine space. Affine transformations preserve the dimension of any affine subspaces meaning that they map voxels to voxels, lines to lines, planes to planes, and so forth. With affine transformations, different views can be generated without inadvertently introducing artifacts which may occur if, e.g., non-affine transformations are applied imprudently, and which may give rise to false classifications. In contrast to affine transformations, non-affine transformations do not preserve the dimensions of affine sub-spaces. As such, non-affine transformations may provide different displacements for one voxel or, in turn, cancel voxels. Nonetheless, non-affine transformations can be very handy if deformed tissue is being analyzed as they allow to reproduce non-affine organ deformations which may occur in connection with patient weight loss or tissue shrinkage or swelling. Non-affine image transformations may be able to compensate for such effects and provide for an undistorted view of the tissue. In order to avoid unwanted artifacts, the application of non-affine transformations may be accompanied by applying mathematical modeling to find a statistic of motion or deformation in considered organs. The models may be based on macroscopic equations of motion as exemplified by the Navier-Cauchy equation.

According to an embodiment, generating the plurality of representations comprises rotating the region of interest, and/or mirroring the region of interest, and/or scaling the region of interest, and/or shearing the region of interest, and/or translating the region of interest in the image space of the image data set, and/or any combination of the aforementioned.

In other words, the image processing steps may be selected from the group including one or more rotation transformations in order to generate processed image data rotated with respect to the original image data by an angle of rotation around an axis of rotation, one or more mirror transformations configured to generate processed image data mathematically reflected with respect to the original image data by a mirror plane, one or more scaling transformations in order to generate up- or down-scaled processed image data, one or more shear transformations in order to generate sheared processed image data, and any combination of the aforethe.

In other words, generating a plurality of different representations may comprise applying a rotation-transformation to image data associated with the region of interest so as to generate a representation with processed image data rotated with respect to the region of interest by an angle around an axis of rotation, and/or applying a reflection-transformation to image data associated with the region of interest so as to generate a representation with processed image data relating to a mirror image of the region of interest with respect to a mirror plane, and/or applying a shear-transformation to image data associated with the region of interest so as to generate a representation with processed image data relating to a sheared image of the region of interest, and/or applying a scaling-transformation to image data associated with the region of interest so as to generate a representation with processed image data relating to a scaled image of the region of interest, and/or applying combinations thereof.

Aforementioned transformations may also be designated as "geometric transformations" in the framework of this application. Using such geometric transformations has the advantage that additional representations can be generated by operations which are comparatively easy to implement and require little computational effort. By consequence, these transformations are particularly suited for an "online" generation of multiple views. At the same time, suchlike geometric transformations yield representations which have proven to be very useful for improving the ensuing classification. For instance, rotating the image data comprised in the region of interest can be conceived as viewing at the data from different angles. In general, all of the transformations may be combined with one another, for instance, by applying them subsequently. For instance, a rotation transformation may be applied first, followed by a mirror transformation and a scaling transformation. The transformations may be applied to all or part of the image data comprised in the region of interest. Moreover, the transformations may also extend to image data outside of the actual regions of interest. Further, the generation of the representation may involve applying a cropping at/around the location of the object/the candidate abnormality. In this regard, cropping may be the final image processing step in order to cut the region of interest to size for generating the representations to be classified. Further, cropping may also be used for the aforementioned translation of the region of interest, as moving a cropping frame relative to the original image data yields different relative positions of an object of potential pathological interest within different representations.

According to an embodiment, the image processing steps comprise rotations of the region of interest at M angles and reflections in K dimensions. According to an embodiment, K may be 3 and M may be selected from an interval between 4 and 24. In particular, M may range from 8 to 16, and preferably may be set to 12.

By using the combination of M angles and reflections in K dimensions, the region of interest may be systematically examined from a variety of viewing directions during classification, thereby improving the classification result.

According to an embodiment, the medical image data set and the region of interest comprise three-dimensional image data. Then, in the step of generating a plurality of representations, the image processing steps at least comprise: a rotation of the region of interest by 90° with respect to an axis of rotation, a rotation of the region of interest by 180° degrees with respect to the axis of rotation, and a rotation of the region of interest by 270° with respect to the axis of rotation, the axis of rotation preferably being one of the main axes spanned by the medical image data set. In other words, the plurality of representations comprise one representation rotated by 90° around the axis of rotation, one representation rotated by 180° around the axis of rotation, and one representation rotated by 270° around the axis of rotation.

Using multiples of 90° as rotation angles and one main axis of the image data arrays as rotation axis has the advantage that the rotations are readily compatible to the data structure of the three-dimensional image data. Since three-dimensional image data is usually provided in the form of arrays of voxels, a rotation by 90° around the one of the axes of the array maps one voxel of the original image data array to precisely one voxel of the processed image data array and does not require data interpolation. At the same time, the rotations by 90°, 180° and 270° enable to view the image data from all sides.

According to an embodiment, in the step of generating a plurality of representations, the image processing steps at least comprise a reflection of the image data along one of main axes spanned by the medical image data set.

The main axes of the medical image data set may be the dimensions of the array of pixels or voxels comprising the image data. If, for instance, three-dimensional image data is considered, the array of voxels has n times m times p voxels. The main axes would be the axes in the n-, m- and p-direction. A reflection along the n-axis would, thus, correspond to a reflection with respect to the m-p-plane of the array as mirror plane.

Reflection transformations along the main axes of the medical image data set have the benefit that they are readily compatible with the underlying data structure which enables a straightforward implementation and reduces computational costs.

According to an embodiment, applying one or more image processing steps comprises applying one or more different cropping frames (to the original image data comprised in the medical image data) for generating different representations.

Different cropping frames may relate to morphological different cropping frames (e.g., rectangular frames vs. quadratic/cubic frames vs. circular/spherical frames) as well as to cropping frames which are differently positioned in the medical image data set. Regarding the latter, it is conceivable that a given cropping frame is translated (moved) multiple times in the medical image data set to generate different sections and therewith representation of a region of interest (of an object). In other words, according to an embodiment, applying one or more different cropping frames comprises using different relative positions of the cropping frames with respect to the object.

Using different cropping frames has the advantage that the image data taken into consideration around a suspicious object can be varied. This may bring about the advantage that the object to be classified may be evaluated in different textural and anatomic contexts.

According to an embodiment, the image processing steps include subjecting image data in (or: of) the region of interest to one or more operations selected from the group of: image smoothing, image sharpening, contrast enhancement, edge enhancement, color filtering, color normalization, grayscale normalization, denoising, blurring, de-blurring histogram equalization, high-pass filtering, low-pass filtering, convolution filtering, deconvolution filtering, and/or any combination of the aforementioned.

In contrast to the more geometric transformations discussed before, the above operations relate to image processing steps for enhancing/improving/manipulating image data without mapping original image data to new locations. For instance, the above operations may be implemented by applying corresponding image filters to the image data to be processed. Like in the case of geometric transformations, the operations may be applied to all or part of the voxels in the region of interest. In addition, the operations may also be applied to regions outside of the region of interest and/or the entire medical image data set. Different representation may be generated by using different operations for different representations. For instance, one representation may result if the original image data is subject to a low-pass filtering while another results by employing a high pass or de-blurring filter.

The usage of such image processing steps has the advantage that imaging artifacts can be reduced. At the same time, by relying on various different image processing operations, the likelihood of systematically introducing new artifacts due may be diminished.

It is explicitly included in this disclosure that the above operations may be combined with all kinds of mathematical (geometric) transformations as introduced or discussed before (including all affine and non-affine transformations). For instance, a representation may be generated by mirroring the image data with respect to some mirror plane and then smoothing the result by an interpolation or blurring step (or filter). Similarly, scaling steps may be accompanied by one or more interpolating steps. To provide another example, contrast and/or image sharpening steps may be carried out prior to generating multiple representations by using a moving cropping frame.

Combining geometric transformations with image filtering operations may bring about an improved error or artifact correction. As an example, the rotation of image data by arbitrary angles may lead to a situation where the transformation result cannot straightforwardly be mapped to a rectangular array of voxels. Here, an interpolation step can be very useful to smooth the result and improve the data for classification.

According to an embodiment, the step of determining a classification for each of the representations comprises using a trained function. Thereby, the trained function is configured to generate a classification for the region of interest (and/or an object/the candidate abnormality comprised in the region of interest) based on a representation of the region of interest.

"Using a trained function" may involve inputting each representation of the plurality of representations into the trained function so that it outputs an (individual) classification for each representation. A trained function, in general, may be seen as mapping input data to output data thereby fulfilling a certain learned task (in this case: deriving a classification on the basis of the input image data). The relation between input and output may be governed by one or more (in general: a plethora) of parameters embedded in the trained function. The values of the parameters may be learned (adapted) during training according to the task the trained function will have to fulfill. Other terms for trained function may be trained mapping specification, mapping specification with trained parameters, function with trained parameters, trained machine learned model, algorithm based on artificial intelligence, intelligent agent, or machine learned algorithm. Applying the trained functions may mean inputting image data (during testing/deployment: the processed image data contained in the representations). The output of the trained function is, in general, indicative of a class, trait, signature or classification of the object. The output may comprise a confidence score pertaining to the pathological relevance of the region of interest (the object contained). Further, the output may be a binary output, e.g., indicating whether or not representation likely relates to an actual abnormality or to a false positive, e.g., in the form of either outputting 1 or 0, or TRUE/FALSE. In addition or as an alternative, the output of the trained function may comprise further diagnostic information with respect to the representation/the object depicted such as a degree of malignancy, a state of the contour (e.g., either smooth or spiculated), a degree of calcification or fat deposition, or degree of solidity, or other pathologically relevant observable of the underlying object.

Preferably, the trained function comprises a neural network, most preferably a convolutional neural network. A neural net is basically built up like a biological neural net, e.g., a human brain. In particular, an artificial neural network comprises an input layer and an output layer. It may further comprise a plurality of layers between input and output layer. Each layer comprises at least one, preferably a plurality of nodes. Each node may be understood as a biological processing unit, e.g. a neuron. In other words, each neuron corresponds to an operation applied to input data. Nodes of one layer may be interconnected by edges or connections, in particular by directed edges or connections, to nodes of other layers. These edges or connections define the data flow between the nodes of the network. In particular, the edges or connections are equipped with a parameter, wherein the parameter is often denoted as "weight". This parameter can regulate the importance of the output of a first node to the input of a second node, wherein the first node and the second node are connected by an edge. In particular, a neural network can be trained. In particular, training of a neural network is performed based on known pairs of input and output values according to a 'supervised learning' technique, wherein the known input values are used as inputs of the neural network, and wherein the corresponding output value of the neural network is compared to the corresponding known output value. The artificial neural network independently learns and adapts the weights for the individual nodes as long as the output values of the last network layer sufficiently correspond to the known output values according to the trainings data. For convolutional neural networks, this technique is also called 'deep learning'. The terms 'neural network' and 'artificial neural network' can be used as synonyms. Most preferably, in the training phase, the convolutional neural network is trained to classify different preferably predefined types of pathological relevant patterns such as lesions, nodules, calcification, emphysema, honey combing, and ground glass opacity (at least as relevant or not relevant). Each disease pattern may be characterized by individual visual image features. Thus, during the training phase, the neural network learns to classify the extracted feature signature to at least one of these disease patterns. During training, manual mapping of individual representation images to individual disease patterns may be applied.

A first group of neural network layers may be applied to extract features from images. In this case, medical images, i.e. the gray scale and/or color values for each individual image element of the image, serve as input values for the neural network. The thus extracted features like, contrast, gradients, texture, density, or the like may be fed as input values to a second group of network layers, also known as classifiers, which serve to further assign objects and/or characteristics to at least one of the extracted features present in the image.

According an implementation, skip connections between layers are used, so that layers may also output to other layers than the sequentially next layer. Such skip connections introduce one or more residual blocks or layers. Using residual blocks results in the ability to train much deeper networks than what was previously possible as this alleviates the vanishing gradient problem known from very deep neural networks.

According to an embodiment, the trained function is based on one of Support Vector Machine, naive Bayes, neural network, decision tree, and/or ResNet. Thereby, Res- Net may be embodied as a convolutional neural network comprising one or more residual blocks or layers.

The inventors have recognized that the above algorithms are suited to derive a classification of an object/a region of interest based on image comprised in a representation thereof.

According to an embodiment, the step of determining an ensemble classification is based on calculating a linear and/or non-linear combination of the plurality of classifications, preferably, in the form of a weighted sum of the plurality of classifications or an average over the plurality of classifications.

The use of linear and/or non-linear combinations has the benefit that the individual contributions of the different representations may be weighted differently according to their relevance. In this regard, non-linear combinations may offer a great degree of freedom to derive an optimal ensemble classification. At the same time, finding the optimal non-linear combination may be more involved. Each summand in the linear and/or non-linear combination may be accorded a weight as a measure of the relevance of the individual classification to the overall result. In the case of a linear combination, this results in a weighted sum. However, for many applications simply calculating the average also provides useful results which are easily traceable for the user.

According to an implementation, the weights may be set based on the respective transformations underlying the corresponding representation.

In doing so, transformations more likely leading to valuable information can be weighed systematically higher than others. Moreover, the calculation of the ensemble classification as such may be dynamically adapted to the case at hand and the image processing steps used.

According to an embodiment, the ensemble classification is calculated using a further trained function on the basis of the plurality of classifications and, optionally, the respectively corresponding image processing steps.

This has the benefit that the optimal way of calculating the ensemble average for the respective set of representations may be determined automatically. For instance, the further trained function may be applied on the plurality of representations and provided with an indication of the image processing steps that where applied on the original data to generate the respective representation. The further trained function may be trained to generate, based on that information, an optimal ensemble classification, e.g., in the form of a specifically adapted weighted non-linear combination of the individual classifications. By using the further trained function, more combinations and weights can be explored as could be done by a human. According to an implementation, the further trained function may be part of the trained function.

According to an embodiment, the trained function is configured such that its outputs respectively comprise a classification score, and the step of determining an ensemble classification is based on calculating a linear and/or non-linear combination of the individual classification scores, optionally, in the form of a weighted sum of the corresponding plurality of classification scores or an average over the corresponding plurality of classification scores. According to an implementation, the classification score may be a confidence score indicating whether or not the region of interest comprises an actual abnormality.

According to an embodiment, the step of determining an ensemble classification involves classifying the candidate abnormality/the region of interest as false positive if the average confidence score is lower than a predetermined threshold.

The usage of a threshold provides an intuitive and easy to implement way of deriving an ensemble classification for the object under consideration. Thereby the threshold may be set by a user or automatically or semi-automatically for users that need more assistance.

According to an implementation, the step of determining an ensemble classification involves generating a result indicative of the pathological relevance of the candidate abnormality/the region of interest, in particular, whether or not the candidate abnormality is malignant of benign/the region of interest contains a malignant or benign object.

This has the advantage that a user is provided with additional medical information for the region of interest/the object under consideration which may be relevant for downstream diagnostic decisions.

According to an embodiment, the step of generating a detection result comprises outputting the detection result in the form of a rendering of the medical image data set, wherein the abnormalities are differently highlighted according to the corresponding ensemble classification.

Providing the user with suchlike assistance image has the benefit that the information gathered is presented in an intuitively accessible manner which helps the user to derive conclusions from the analysis and take suitable decisions. Hereby, "highlighting according to the ensemble classification" may mean that false positives are not highlighted/shown at all. Vice versa, actual abnormalities may be indicated with a color to focus the attention of the user to these regions of the medical image data set.

The step of generating a detection result may comprise eliminating one or more of the candidate abnormalities from the set of candidate abnormalities on the basis of the corresponding ensemble classifications.

This has the benefit that candidate abnormalities may be automatically disregarded, if their ensemble classification indicates that their pathological relevance does not warrant further investigation. In particular, candidate abnormalities may be disregarded if the classification indicates that they relate to false positives. This decreases the workload of the user as she or he can focus on the relevant findings.

According to an embodiment, the step of determining a set of candidate abnormalities comprises: applying a candidate generation function to the medical image data set, the candidate generation function being configured such that it detects one or more candidate abnormalities in the medical image data set, which candidate abnormalities are indicative of a possibly pathological relevant change in the body part.

According to a further embodiment, the candidate generation function is a trained function/an intelligent agent.

According to another embodiment, the inventive idea may also be employed for general image processing outside of the medical context. For such applications as well, the proposed data augmentation by generating multiple representations of an object to be classified helps to reduce systematic errors and improves the accessibility of image features for classification. Accordingly, the classification result is more accurate and reliable. In the light of this, according the aspect, a method for classifying a region of interest in an image data set is provided, which method comprises a plurality of steps. One step is directed to generating a plurality of different representations of the region of interest. Another step is directed to determine, for each of the representations, a classification to generate a corresponding plurality of classifications. Another step is directed to calculate an ensemble classification for the region of interest based on the plurality of classifications.

Moreover, according to another embodiment, the data augmentation may also be used during training a trained function for classifying objects in computer aided diagnosis of medical image data sets depicting a body part of a patient. Such method includes the steps of: providing a training data set, wherein the training data set includes: training image data relating to an image volume containing an object to be classified; and a target classification of the object; generating N>1 different representations of the object, each of the N different representations comprising processed image data generated by applying one or more image processing steps to the training image data, generating a classification of the object by applying the trained function to one of the representation, comparing the classification with the target classification, and adjusting the trained function as a function of the comparison.

According to the above embodiment, the data augmentation is used to increase the amount of training data. Especially in situations where the availability of training data is limited, this may facilitate the training process yielding better classifiers.

According to an embodiment, a system for detecting pathologically relevant abnormalities in a medical image data set depicting a body part of a patient is provided. The system comprises an interface unit for receiving a medical image data set. Further the system comprises a computing unit configured to determine a set of candidate abnormalities in the medical image data set. The computing unit is further configured to generate, for each of the candidate abnormalities comprised in the set of candidate abnormalities, a plurality of different representations of the respective candidate abnormality. The computing unit is further configured to determine, for each of the candidate abnormalities comprised in the set of candidate abnormalities, a corresponding plurality of classifications, wherein each of the classifications corresponds to one of the plurality of representations. Further, the computing unit is configured to determine, for each of the candidate abnormalities comprised in the set of candidate abnormalities, an ensemble classification of the respective candidate abnormality based on the plurality of classifications. Finally, the computing unit is configured to generate a detection result using the ensemble classifications.

According to an embodiment, the system is adapted to implement embodiments of the inventive method for detecting pathologically relevant abnormalities in a medical image data set. The computing unit may comprise a candidate generation unit configured to detect a set of candidate abnormalities. The candidate generation unit may be configured to provide indications of the candidate abnormalities, e.g., in the form of the coordinates of the respective candidate abnormality in the medical image data set. In addition to that or as an alternative, the indications provided by the candidate generation unit may comprise the dimensions of the candidate abnormality (e.g., as the diameter or the volume of the candidate abnormality). The candidate generation unit may be seen as the detection stage of the system.

The computing unit may further comprise a data augmentation unit configured to generate a plurality of representations for each of the candidate abnormalities so that each of the plurality of representations of a candidate abnormality provides a different view of the candidate abnormality. In order to generate the different representations, the data augmentation unit may be configured to process the image data at least in a vicinity around the candidate abnormality so that differently processes image data results for each representation. To this end, the data augmentation unit may input, e.g., the coordinates of a candidate abnormality and apply different image processing steps to the image data in a vicinity (region) around the coordinates. The data augmentation unit may further be configured to generate an image patch/volume suited for further processing by cropping the (processed) image data at the coordinates of the candidate abnormality. Cropping may be performed before and/or after image processing.

The computing unit may further comprise a classifier unit configured to output a classification for each representation, the classification being indicative of the pathological relevance of the candidate abnormality comprised in the representation. To this end, the classifier unit may be configured to run an appropriate classifying function.

The computing unit may further comprise a result generation unit configured to generate an ensemble classification per candidate abnormality based on the respective individual classifications output by the classifier unit.

The data augmentation unit, the classifier unit and the results generation unit together may be seen as constituting the filter stage of the system.

The computing unit may be realized as a data processing system or as a part of a data processing system. Such a data processing system can, for example, comprise a cloud-computing system, a computer network, a computer, a tablet computer, a smartphone and/or the like. The computing unit can comprise hardware and/or software. The hardware can comprise, for example, one or more processors, one or more memories and combinations thereof. The one or more memories may store instructions for carrying out the method steps according to an embodiment of the invention. The hardware can be configurable by the software and/or be operable by the software. Generally, all units, sub-units or modules may at least temporarily be in data exchange with each other, e.g., via a network connection or respective interfaces. Consequently, individual units may be located apart from each other.

The interface unit may comprise an interface for data exchange with a local server or a central web server via internet connection for receiving the reference image data or follow-up image data. The interface unit may be further adapted to interface with one or more users of the system, e.g., by displaying the result of the processing by the computing unit to the user (e.g., in a graphical user interface) or by allowing the user to adjust parameters for image processing and/or to select the candidate abnormalities.

According to another embodiment, the invention further relates to an image analysis system comprising the system for detecting pathologically relevant abnormalities in a medical image data set and a medical image system configured to acquire, store and/or forward follow-up medical images (comprising the reference image data and the follow-up image data). Thereby, the interface unit is configured to receive the medical image data set from the medical image system.

According to an embodiment, the medical image system comprises one or more archive stations for storing medical image data sets, which may be realized as a cloud storage or as a local or spread storage, e.g., as a PACS (Picture Archiving and Communication System). Further, the medical image system may comprise one or more medical imaging modalities, such as a computed tomography system, a magnetic resonance system, an angiography (or C-arm X-ray) system, a positron-emission tomography system, a mammography system, system for acquiring digital pathology images or the like.

According to another embodiment, the present invention is directed to a computer program product comprising program elements which induce a computing unit of a system for detecting pathologically relevant abnormalities in a medical image data set to perform the steps according to an embodiment of the above method, when the program elements are loaded into a memory of the computing unit.

According to another embodiment, the present invention is directed to a computer-readable medium on which program elements are stored that are readable and executable by a computing unit of a system detecting pathologically relevant abnormalities in a medical image data set, in order to perform steps of an embodiment of the inventive method, when the program elements are executed by the computing unit.

The realization of an embodiment of the invention by a computer program product and/or a computer-readable medium has the advantage that already existing providing systems can be easily adopted by software updates in order to work as proposed by an embodiment of the invention.

The computer program product can be, for example, a computer program or comprise another element next to the computer program as such. This other element can be hardware, e.g., a memory device, on which the computer program is stored, a hardware key for using the computer program and the like, and/or software, e.g., a documentation or a software key for using the computer program. The computer program product may further comprise development material, a runtime system and/or databases or libraries. The computer program product may be distributed among several computer instances.

FIG. 1 depicts a system for classifying one or more objects in a medical image data set MID according to an embodiment of the present invention. The system is adapted to perform the method according to one or more embodiments, e.g., as further described with reference to FIGS. 2 and 3.

The system comprises a user interface 10 (as part of the interface) and a processing system 20 (as part of the processor). Further, the system may comprise a medical image system 40 for acquiring, storing and/or forwarding medical image data or medical image data sets MID. Such medical image data sets MID may be loaded from the medical image system 40, e.g., by the processing system 20 or by the user interface 10 directly.

Medical image data sets MID may be three-dimensional image data sets acquired, for instance, using a computed tomography system or a magnetic resonance imaging system. The image information is encoded in a three-dimensional array of m times n times p voxels. The main axes of the array (and the medical image data set MID) are the axes in the m, n, and p direction. Further, medical image data sets MID may relate to two-dimensional medical images, for instance, acquired with an X-Ray facility, with the image information being encoded in an array of m times n pixels. An ensemble of voxels or pixels may be designated as image data (processed and original image data) in the following. In general, any imaging modalities and scanners may be used, such as ultrasound, x-ray, angiography, fluoroscopy, positron emission tomography, single photon emission computed tomography, or others. Generally, medical image data set MID shows a body part of a patient. The body part depicted in medical image data set MID will comprise various anatomies and organs. Considering the chest area as body part, medical image data set MID might, for instance, depict the lung lobes, the rib cage, the heart, lymph nodes, and so forth. Medical image data sets MID may be formatted according to the DICOM format. DICOM (=Digital Imaging and Communications in Medicine) is an open standard for the communication and management of medical imaging information and related data in healthcare informatics. DICOM may be used for storing and transmitting medical images and associated information enabling the integration of medical imaging devices such as scanners, servers, workstations, printers, network hardware, and picture archiving and communication systems (PACS). It is widely adopted by clinical syndicates, hospitals, as well as for smaller applications like doctors' offices or practices. A DICOM data object consists of a number of attributes, including items such as patient's name, ID, etc., and also special attributes containing the image pixel data and metadata extracted from the image data.

The medical image data set MID generally has an intrinsic resolution determined by the imaging modality and imaging procedure used. Subsequently, the intrinsic resolution may also be denoted as the maximal or initial resolution. Starting from the intrinsic resolution, further resolutions may be calculated by down-sampling the original image data comprised in the medical image data set MID to lower resolutions or up-sampling the original image data comprised in the medical image data set MID to higher resolutions.

User interface 10 comprises a display unit 11 and an input unit 12. User interface 10 may be embodied by a mobile device such as a smartphone or tablet computer. Further, user interface 10 may be embodied as a workstation in the form of a desktop PC or laptop. Input unit 12 may be integrated in display unit 11, e.g., in the form of a touch screen. As an alternative or in addition to that, input unit 12 may comprise a keyboard, a mouse or a digital pen and any combination thereof. Display unit 11 is configured for displaying representations of the medical image data set MID and/or the result of the object classification as performed by processing system 20.

User interface 10 further comprises an interface computing unit 13 configured to execute at least one software component for serving display unit 11 and input unit 12 in order to provide a graphical user interface for allowing the user to select the medical image data MID to be further analyzed and instruct the processing unit 20 accordingly, e.g., within the graphical user interface. In addition, interface computing unit 13 may be configured to communicate with medical image system 40 or processing system 20 for receiving the medical image data set MID and/or the result of the image processing to be displayed to the user. The user may activate the software component via user interface 10 and may acquire the software component, e.g., by downloading it from an internet application store. According to an example, the software component may also be a client-server computer program in the form of a web application running in a web browser. The interface computing unit 13 may be a general processor, central processing unit, control processor, graphics processing unit, digital signal processor, three-dimensional rendering processor, image processor, application specific integrated circuit, field programmable gate array, digital circuit, analog circuit, combinations thereof, or other now known device for processing image data.

Processing system 20 may comprise sub-units 21-24 configured to process medical image data sets MID for classifying objects comprised in medical image data set MID. Processing system 20 may be an image processor. The image processor may be a general processor, central processing unit, control processor, graphics processing unit, digital signal processor, three-dimensional rendering processor, image processor, application specific integrated circuit, field programmable gate array, digital circuit, analog circuit, combinations thereof, or other now known device for processing image data. The image processor is a single device or multiple devices operating in serial, parallel, or separately. The image processor may be a main processor of a computer, such as a laptop or desktop computer, or may be a processor for handling some tasks in a larger system, such as in the imaging system or the server. The image processor is configured by instructions, design, hardware, and/or software to perform the steps discussed herein. Alternatively, processing system 20 may comprise a real or virtual group of computers like a so called 'cluster' or 'cloud'. Such server system may be a central server, e.g., a cloud server, or a local server, e.g., located on a hospital or radiology site. Further, processing system 20 may comprise a memory such as a RAM for temporally loading the medical image data set MID and/or any representations derived therefrom for further processing. Alternatively, such memory may as well be comprised in user interface 10. Additionally, processing system 20 may comprise a database 27 for the local storage of medical image data sets MID, representations R1 . . . RN derived therefrom and/or image processing tools.

Sub-unit 21 is an object identification module or unit. As it is configured to identify one or more candidate abnormalities CA and/or regions of interest containing a candidate abnormality (e.g., in the form of one or more candidate volumes) it may also be designated as candidate generation module. Candidate abnormalities CA thereby may relate to suspicious image patterns or objects. "Suspicious" may mean that they bear a certain likelihood of relating to a pathologically relevant change in the body part under investigation. For instance, candidate abnormalities CA may relate to objects which are likely to be classified as lesions, nodules, masses, polyps, calcifications and the like. The output of sub-unit 21 may be in the form of the coordinates of candidate abnormalities CA in the medical image data set MID (e.g., the center-point coordinates of candidate abnormalities CA). Further, the output may comprise the dimensions of the candidate abnormalities CA in terms of their size, such as the diameter or volume of the candidate abnormality CA. Another possible output would be in the form the image data in a region of interest defined around candidate abnormality CA. The region of interest thus may represent an area or an image volume within the depicted body part of the patient, which is of specific interest for the user. The region of interest comprises or covers a suspicious or potentially abnormal anatomical structure or object like a lesion or a calcification or the like in the form a candidate abnormality. The region of interest may cover additional neighboring tissue representing unsuspicious areas for providing additional contextual information. Sub-unit 21 may be configured to identify candidate abnormalities CA automatically. To do so, sub-unit 21 may be configured to run a function (a candidate generation function) capable of processing the medical image data set MID to identify candidate abnormalities CA/regions of interest. According to an alternative implementation, sub-unit 21 may also be configured to assist a user in the manual identification of candidate abnormalities CA. To this end, sub-unit 21 may launch an application enabling the user to pinpoint suspicious objects or image volumes at user interface 10. For instance, such application may be configured such that a user may indicate a suspicious image volume by interactively setting a frame or other delineation or by clicking at a suspicious pattern in a representation of the medical image data set MID displayed at user interface 10.

Sub-unit 22 is a data augmentation module or unit configured to generate multiple representations R1 . . . . RN of each object (candidate abnormality CA) identified by the candidate generation module embodied by sub-unit 21. It is an idea of the present invention that each of the representations R1 . . . . RN thus generated provides a different view of the object and the region of interest around the object. In order to generate the different representations R1 . . . . RN, sub-unit 22 may employ image processing tools which transform the original image data in a suspicious image volume containing the candidate abnormality CA into processed image data. In other words, each representation R1 . . . . RN may be seen as containing processed image data associated to a region of interest around a candidate abnormality. The image processing tools used to generate the processed image data may range from mathematical operators to image filters. As will be further detailed below, the mathematical operators may subject the original image data to affine or non-affine transformations in order to generate processed image data. Image filters may relate to image enhancement filters such as denoising, deblurring, or contour sharpening filters. Moreover, image processing tools may comprise routines for up-or downsampling the original image data. Another family of image processing tools may relate to cropping or segmentation tools for constricting the image data (the representations) to a certain image volume prior to classification. According to an implementation, two or more image processing tools may be combined or applied sequentially for generating processed image data. For instance, a mathematical operator may be combined with an image filter (so that, e.g., the original image data is first flipped in one dimension and then deblurred). Of note, one of the representations generated may also be subjected to an identity transformation, so that the processed image data of the identity representation is identical to the original image data (apart from cropping it according to a desired format if required).

Sub-unit 23 is a classification module or unit configured to generate an object-classification C1 . . . CN per representation R1 . . . RN. The object-classification can be conceived as a classification C1 . . . CN of the object (the candidate abnormality CA) or the region of interest containing the object in view of the respective representation R1 . . . RN. Sub-unit 23 complements the candidate generation module 21 in that it assesses (classifies) the objects identified as candidate abnormalities CA according to pathological relevance. This may involve classifying candidate abnormalities CA as relevant or irrelevant, as relating to an actual abnormality (in a pathological or medical sense) or as a false positive, as malignant or benign, and so forth. In order to fulfill this task, sub-unit 23 may run a trained function TF which has been trained to output a classification based on image data depicting the object to be classified (i.e., the candidate abnormalities CA). Despite the classification result depends on the processed image data comprised in the respective representation R1 . . . RN, sub-unit 23 is in principle independent of the sub-unit 22. Specifically, sub-unit 23 is generally capable of processing any representation (provided that it is of suitable format) no matter which image processing tools the representation has been subjected to and what candidate abnormality CA is being looked at. Individual classifications C1 . . . CN of one and the same object CA are generated independently from one another on the basis of the individual representations R1 . . . RN.

In sub-unit 24, these individual, representation-based classifications C1 ... CN are combined to generate ensemble classifications EC for each of the candidate abnormalities CA identified by sub-unit-21. Thus, sub-unit 24 may be conceived as a results generation module. Sub-unit 24 may further be configured to translate or convert the ensemble classifications EC into a result suitable for a user or for further processing. This may mean that false positives are disregarded. This may further mean that the ensemble classification EC—be it in the form of a score or a binary marker—is output to the user. The result may be in the form of one or more assistance images AI in which the candidate abnormalities CA are visually highlighted according to their ensemble classification EC. This may mean that the candidate abnormalities CA are colored according to the ensemble classification EC and/or supplemented with a brief textual description. Sub-unit 24 may further be configured to associate the ensemble classifications EC to the medical image data sets MID either by encoding this information in the data set directly (e.g., by using a suited DICOM field) or by generating an appropriate supplementary data file which may be associated to the medical image data set MID using appropriate electronic data identifiers (such as the patient ID and/or the accession number of the underlying examination). Sub-unit 24 may further be configured to archive the information gathered by sub-units 21-23 in the archive and review station 42.

The designation of the distinct sub-units 21-24 is to be construed by way of example and not as limitation. Accordingly, sub-units 21-24 may be integrated to form one single unit (e.g., in the form of "the processor") or can be embodied by computer code segments configured to execute the corresponding method steps running on a processor or the like of processing system 20. The same holds true with respect to interface computing unit 13. Each sub-unit 21-24 and interface computing unit 13 may be individually connected to other sub-units and or other components of the system where data exchange is needed to perform the method steps. For example, sub-units 21 and 24 may be connected, via an interface 26, to the medical image system 40 for retrieving the medical image data set MID and/or to interface computing unit 13 for forwarding/showing the assistance image AI to the user via user interface 10. Processing system 20 and interface computing unit 13 together may constitute the processor. Of note, the layout of the processor, i.e., the physical distribution of interface computing unit 13 and sub-units 21-24 is, in principle, arbitrary. For instance, sub-unit 24 (or individual elements of it or specific algorithm sequences) may likewise be localized in user interface 10. The same holds true for the other sub-units 21-23. Specifically, processing system 20 may also be integrated in user interface 10. As already mentioned, processing system 20 may alternatively be embodied as a server system, e.g., a cloud server, or a local server, e.g., located on a hospital or radiology site. According to such implementation, user interface 10 could be designated as "frontend" or "client" facing the user, while processing system 20 could then be conceived as "backend" or server. Communication between user interface 10 and processing system 20 may be carried out using the https-protocol, for instance. The computational power of the system may be distributed between the server and the client (i.e., user interface 10). In a "thin client" system, the majority of the computational capabilities exists at the server. In a "thick client" system, more of the computational capabilities, and possibly data, exist on the client.

Medical image system 40 is generally configured for acquiring and/or storing and/or forwarding medical image data sets MID. For instance, medical image system 40 may comprise an archive/review station 42 for storing reference image data RI and/or follow-up image data FI. Archive/review station 42 may be realized as a cloud storage. Alternatively, archive/review station 42 may be realized as a local or spread storage, e.g., as a PACS (Picture Archiving and Communication System). Archive/review station 42 may further store further clinical information related to medical image data sets MID, wherein the clinical information may comprise, e.g., related medical findings, personal information related to the patient under consideration, patient records or the like. Alternatively, a further database (not shown) may store this related information. Further, medical image system 40 may comprise a medical imaging modality 41, such as a computed tomography system, a magnetic resonance system, an angiography (or C-arm X-ray) system, a positron-emission tomography system, a mammography system, system for acquiring digital pathology images or the like.

Individual components of the system may be at least temporarily connected to each other for data transfer and/or exchange. User interface 10 communicates with processing system 20 via an interface 26 to exchange, e.g., medical image data set MID or the result of the computation, e.g., in the form of assistance image AI. For example, processing system 20 may be activated on a request-base, wherein the request is sent by user interface 10. Further, processing system 20 may communicate with medical image system 40 in order to retrieve one or more medical image data sets. As an alternative or in addition to that, user interface 10 may communicate with medical image system 40 directly. Medical image system 40 and, in particular, archive/review station 42, may likewise be activated on a request-base, wherein the request is sent by processing system 20 and/or user interface 10. Interface 26 for data exchange may be realized as hardware- or software-interface, e.g., a PCI-bus, USB or fire-wire. Data transfer may be realized using a network connection. The network may be realized as local area network (LAN), e.g., an intranet or a wide area network (WAN). Network connection is preferably wireless, e.g., as wireless LAN (WLAN or Wi-Fi). Further, the network may comprise a combination of different network examples. Specifically, the network may comprise a network compatible with the DICOM-standard (Digital Imaging and Communications in Medicine) and the retrieval of the medical image data set MID may be carried out by a DICOM query and retrieve application class. Likewise, archiving the assistance image AI in medical image system 40 may be carried out using the DICOM query and retrieve application class. Interfaces for data exchange together with the components for interfacing with the user may be regarded as constituting the aforementioned interface.

Figure 2:
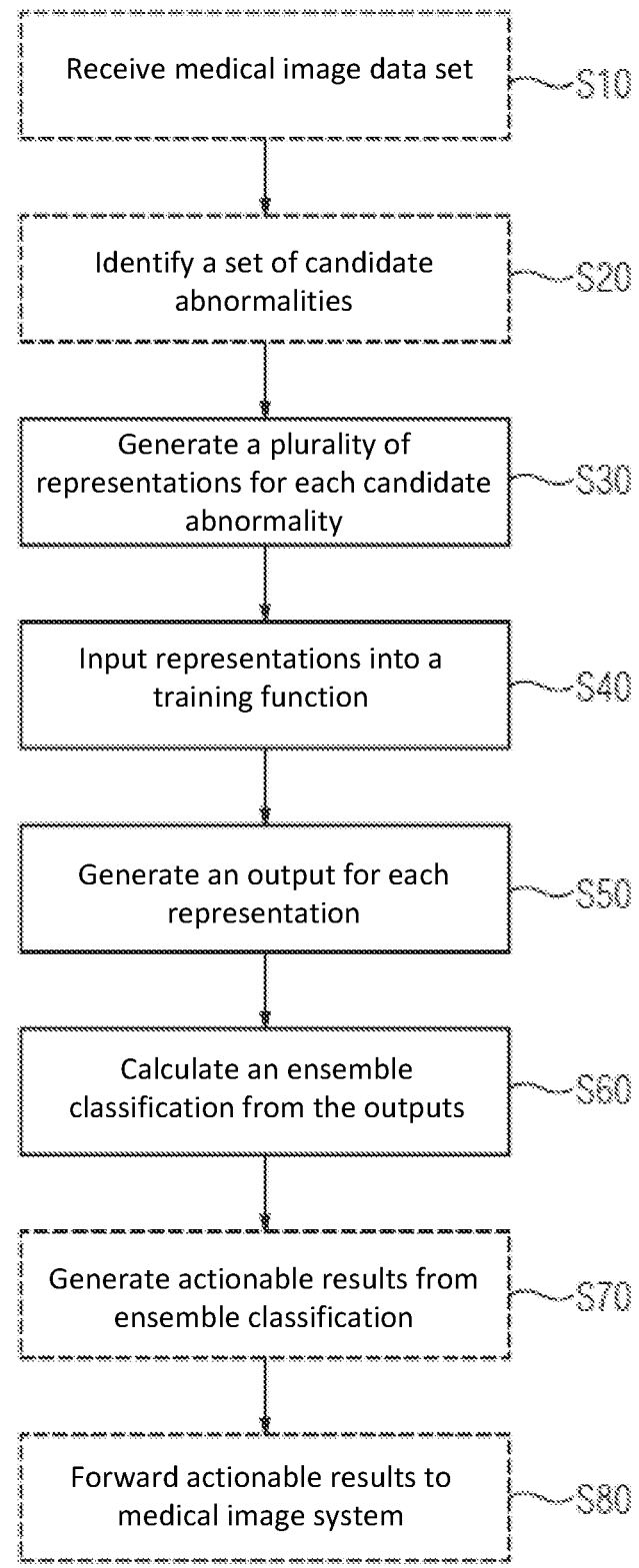
FIG. 2 depicts a flowchart illustrating a method classifying one or more objects in a medical image data set according to an embodiment, FIG. 3 schematically shows data streams associated with a method classifying one or more objects in a medical image data set according to an embodiment.
Figure 3:
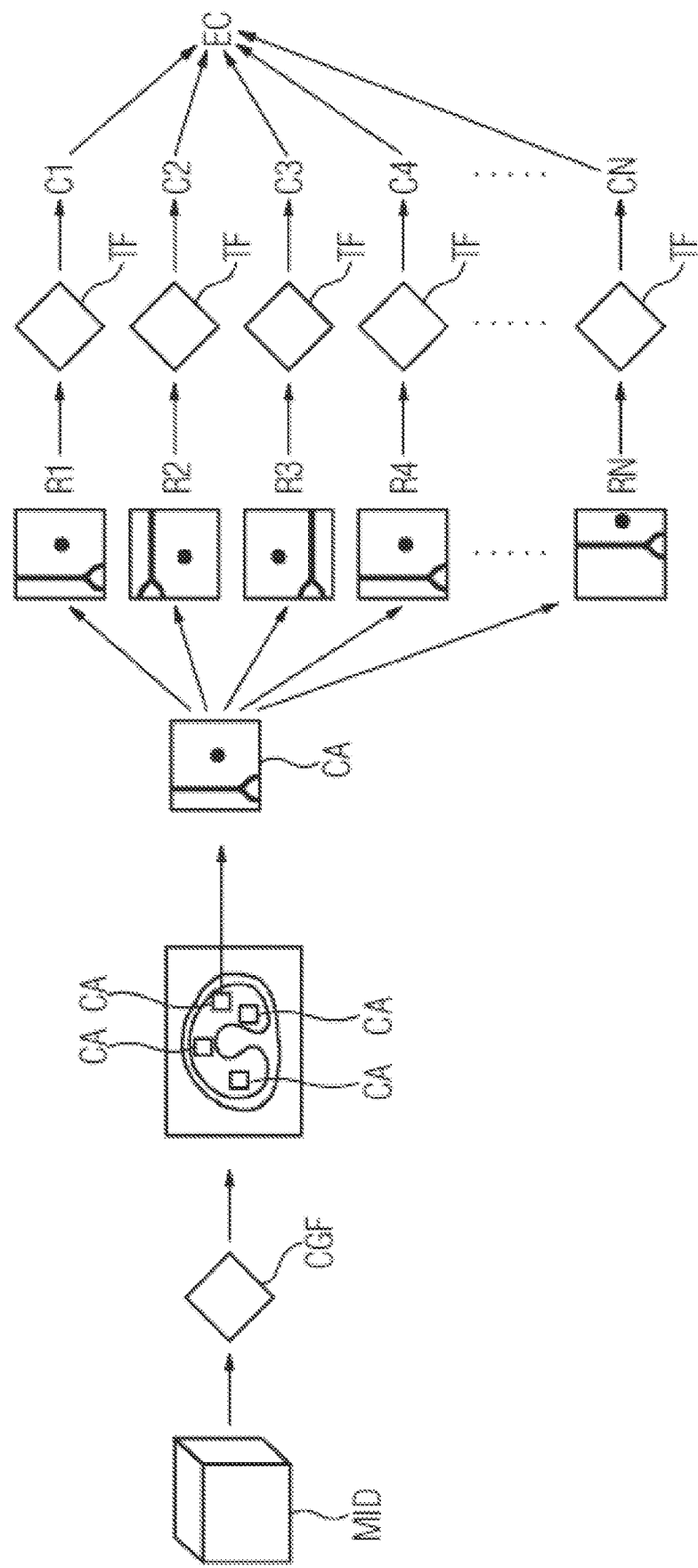

FIG. 2 depicts an inventive method for classifying objects CA in medical image data sets MID according to an embodiment of the present invention. Corresponding data streams are illustrated in FIG. 3. The method comprises several steps. The order of the steps does not necessarily correspond to the numbering of the steps but may also vary between different embodiments of the present invention. Optional steps are shown with dashed frames in FIG. 2.

The method depicted in FIG. 2 is directed to a computer aided detection (CADe) and/or computer aided diagnosis (CADx) workstream. While CADe workstreams are directed to securely flag out abnormalities with the least number of false positives possible, CADx workstreams are set out to provide additional information on the identified abnormalities such as whether they are malignant or benign. The workflow illustrated in FIGS. 2 and 3 may provide both functionalities, CADe and CADx, with CADx being an optional add-on, however.

In principle, the workflow can be divided into two main parts: the detection of candidate abnormalities (objects) CA according to steps S10 to S30, and the further processing of the candidate abnormalities CA in order to identify false positives (or, in other words, determine whether or not a candidate abnormality CA is an actual abnormality) according to steps S40 to S70. Of note, steps S10 to S30 are optional steps as the initial identification of the candidate abnormalities CA may be performed independent of their further analysis according to the inventive method. For instance, the identification of candidate abnormalities CA may be performed by a separate computer-implemented method outside of the scope of the present application. Likewise, it is conceivable that the candidate abnormalities CA are directly identified by a user, e.g., by manually defining one or more regions of interest around suspicious objects in the image study MID currently under review.

In a first optional step S10, the medical image data set MID to be analyzed is received (or provided). This may involve selecting medical image data set MID, e.g., stored in the medical image system 40. The selection may be performed manually by a user, e.g., by selecting appropriate image data sets MID in a graphical user interface running in the user interface 10. Moreover, the selection may be carried out automatically, e.g., on a request base as a preprocessing step for further image processing operations, or semiautomatically by the system. In particular, this may involve automatically querying appropriate databases for one or more medical image data sets MID of an examination currently under review by the user. Step S10 may be performed at least partially either on user interface 10 or on processing system 20. Corresponding data exchange is included in this step where necessary.

At subsequent optional step S20, a set of candidate abnormalities CA (or objects) is identified. As mentioned, this can be done manually by a user by marking suspicious objects in the image data via the user interface 10. In FIG. 1, such user selected candidate abnormalities are designated as US-CA for clarification, but otherwise simply referred to as CA. To this end, the user may set a region of interest around the object or point at the object, e.g., by using input unit 12. However, according to an embodiment, the identification or recognition of the candidate abnormalities CA is performed automatically by applying a candidate generation function CGF to the received medical image data MID. The candidate generation function CGF, in general, may be seen as a computer-implemented method or algorithm configured to process the medical image data set MID in order to output indications of one or more candidate abnormalities CA (if any). Thereby, the indications may be coordinates and/or dimensions of the candidate abnormalities CA in the medical image data set MID and/or regions of interest around the candidate abnormalities CA. In principle, a plethora of functionalities and methods is known for the computer aided detection of candidate abnormalities CA—all of which may be implemented in the candidate generation function CGF. For instance, reference is made to US 2009/0 092 300 A1, US 2009/0 067 693 A1, and US 2016/0 321 427 A1, the contents of which are incorporated herein in their entirety by reference. In particular, candidate generation function CGF may comprise one or more trained functions trained to output a set of candidate abnormalities CA if applied to a medical image data set MID. Suitable trained functions for this task include (artificial) neural networks, such as convolutional neural networks. Optional pre-processing steps may be employed to improve the detection results of the candidate generation function CGF. Pre-processing steps may include image enhancement steps such as contrast enhancement, deblurring, auto-alignment, and image segmentation steps in order to distinguish the anatomy of interest (e.g., lung, liver, etc.) from background. According to an embodiment, Step S20 is performed predominately in processing system 20. If user interactions are involved (e.g., if part or all of the candidate abnormalities CA are selected by the user), processing of step S20 may also involve user interface 10. Corresponding data exchange is included in this step where necessary.

According to an implementation, step S20 may be performed with a comparably high sensitivity. This has the benefit that also slight deviations from "normal" are detected which is often required for the comprehensive identification of all pathological relevant changes in a body part and the reduction of false negatives. At the same time, high sensitivities may result in an increased number of false positives, however. As mentioned, false positives do not relate to actual abnormalities in a pathological sense. Such false positives may, for instance, stem from imaging artifacts such as variations in contrast or boundary effects between different anatomies, motion compensation artifacts, artifacts caused by magnetic field inhomogeneities in MRI. Likewise, image features which are somehow reminiscent to pathological abnormalities but otherwise normal or "healthy" may give rise to false positives. For instance, a bifurcation in a blood vessel may be misinterpreted as a lesion under some viewing angles. Steps S30 to S60 are devoted to identify false positives in the candidate abnormalities CA. Optionally, depending on the specific implementation, Steps S30 to S60 may be used to derive additional (diagnostic) information pertaining to the candidate abnormalities CA, such as whether or not a candidate abnormality CA is malignant. Preferably, steps S30 to S60 are performed for each candidate abnormality CA identified at step S20.

At step S30, a plurality of representations R1 . . . RN is generated for each candidate abnormality CA/each region of interest. Each representation R1 . . . RN may be seen as corresponding to a different view of the underlying candidate abnormality CA/the region of interest. It is an idea of the present invention to use the plurality of representations R1 . . . RN to broaden the basis for a decision regarding whether or not a candidate abnormality CA embedded in a region of interest is an actual abnormality or a false positive. Since a candidate abnormality CA may show signs of an actual abnormality in some representations R1 . . . RN and signs of a false positive in other representations R1 . . . RN, factoring in several different representations R1 . . . RN of the region of interest thus increases the likelihood of a correct classification EC of the candidate abnormalities CA. The number N of representations R1 . . . RN may be set flexibly according to requirements of the case at hand. In principle any number N 2 may be used. While for some studies, a small number of representations R1 . . . RN between 2 and 8 may be sufficient, more complex data sets might require a higher number of representations R1 . . . RN between 24 and 32 or more. According to an embodiment, a number between 8 and 24 is used, wherein 10<N<16 has proven to represent a good tradeoff between computation speed and accuracy. According to an embodiment, the number N of representations R1 . . . RN may be interactively set by the user. To this end, the user interface 12 may run an appropriate dialogue, e.g., in the form of a graphical user interface, with which the user may set the number N of representations R1 . . . RN. As an alternative, the number N of representations R1 . . . RN may be preset (according to some examples to N=10, 11, 12, 13 or 14). As yet a further alternative, N may be set automatically by the method, e.g., depending on the study at hand and the task to be performed. For identifying nodules in lung tissue N=12 may be set automatically, for instance. Further, N may be set semi-automatically by making a suggestion to the user which she or he may accept or alter.

Any representation R1 . . . RN of a candidate abnormality CA/the region of interest may comprise a view of the candidate abnormality CA as such and some tissue surrounding the candidate abnormality CA. According to an implementation, each representation R1 . . . RN may be constricted (cropped) to an image patch/volume around the candidate abnormality CA in the respective view. Each representation R1 . . . RN of a candidate abnormality CA comprises image data derived from the original image data comprised in the medical image data set MID. Thus, representations R1 . . . RN may be seen as comprising processed image data. The different representations R1 . . . RN of each candidate abnormality CA/region of interest may be obtained by applying different image processing steps to the original image data at least in an image volume around the candidate abnormality CA under consideration. The original image data thereby may be the image data comprised in the region of interest. Alternatively, the image data subjected to one or more image processing steps may extend beyond the region of interest or correspond to only parts of the region of interest. For example, different representations R1 . . . RN may be obtained by differently cropping the original image data around a candidate abnormality CA. This is exemplified by representations RN and R1 in FIG. 3, where representation RN shows a slightly different image volume than R1. Mathematically, employing different positions of a cropping frame may be conceived as a translation of the field of view. As an alternative, morphological different cropping frames may be used (such as a rectangle for one representation as opposed to a trapezoid for another). Further, different scales or resolutions may be used for generating different representations R1 . . . RN. Here, up- or downscaling the image patch/volume under consideration is an option. In addition, the original image data may be subjected to rotation transformations (c.f., representation R2 and R3) and/or reflection transformations (c.f. representation R3 in FIG. 3). As regards rotations and reflections, arbitrary angles of rotation, rotation axes and mirror planes are possible. According to an implementation, the main coordinate axes in m-, n-, and p-direction may be used to as rotation axes and the angles of rotation may be multiples of 90° as this facilitates the computation. Likewise, reflections may be such that they are performed with respect to the main coordinate axes (e.g., such that the main coordinate axes are perpendicular to the mirror planes). Another possibility for generating different representations R1 . . . RN may be shearing the original image data to obtain one or more sheared representations. The aforementioned transformations—translation, rotation, scaling, reflections, shear—may be subsumed under geometric or affine transformations. Of note, it is not required that the transformations are homogenously applied to the original image data. Rather, it is conceivable to rely on inhomogeneous scaling or shear transformations, where a gradient field of varying shear or scaling factors is applied to the original image data. On a more general scope, this leads to non-affine transformations which may also be used for generating one or more representations R1 . . . RN from the original image data. Non-affine transformations may, for instance, provide different displacements for each voxel of the image data to be processed and can, for example, use non-linear transformations, in which the coordinates of data points in the original image data are subject to flexible deformations in order to generate processed image data. In this regard, one or more distortion filters may be defined. Besides geometric transformations also other types of image processing routines may be used. This comprises denoising (such as high- or low-pass filters, blur-filters), contrast or color enhancement, histogram equalization, image smoothing, edge enhancement, interpolation between pixels/voxels, convolution filters, deconvolution filters and/or image sharpening.

Importantly, the abovementioned image processing steps may be combined to generate new image processing steps. For instance, a rotation transformation may be combined with a reflection transformation, as exemplified by representation R3 in FIG. 3. To provide another example, original image data comprising a candidate abnormality CA may first be subjected to a rotation transformation by an arbitrary angle around a arbitrary axis of rotation using voxel interpolation. That followed, the resulting image data may be cropped for bringing it into a shape readily usable for the ensuing classification in steps S40 and S50. According to an embodiment, Step S30 is performed predominately in processing system 20. If user interactions are involved (e.g., for selecting the number N of representations R1 . . . RN), step S20 may also involve user interface 10. Corresponding data exchange is included in this step where necessary.

At step S40, the representations R1 . . . RN generated for a candidate abnormality CA are input into trained function TF. As can be seen from FIG. 3, each of the representations is input into trained function TF and processed independently by trained function TF. Pre-processing steps may be carried out at this instance if required. Such pre-processing steps may include bringing the representations R1 . . . RN into the right size and resolution. According to an embodiment, Step S40 is performed predominately in processing system 20.

At step S50, trained function TF generates an output C1 . . . CN for each of the representations R1 . . . RN. In other words, if N representations are provided, N outputs C1 . . . CN are generated such that every representation R1 . . . RN gets a vote. Thereby, trained function TF is configured to independently process the representations R1 . . . RN such that N independent outputs C1 . . . CN are generated for each candidate abnormality CA. Each output C1 . . . CN is meant to provide an indication of how to classify the view of the candidate abnormality CA in the representation R1 . . . RN in the underlying medical context. Primarily, the output can be conceived as a statement as to whether the candidate abnormality CA is an actual abnormality or a false positive. Accordingly, each output C1 . . . CN may be regarded as a classification result or classification on its own. In other words, N classifications C1 . . . CN are obtained for each candidate abnormality CA by way of the N outputs C1 . . . CN. In general, different types of output C1 . . . CN are possible dependent on configuration and training of trained function TF. According to one implementation, outputs C1 . . . CN may be binary outputs indicating whether or not a candidate abnormality CA in its respective representation R1 . . . RN likely relates to a false positive, e.g., in the form of either outputting 1 or 0, or TRUE or FALSE, etc. According to another implementation, output C1 . . . CN may be in the form of a more continuous score indicating the likelihood of a false positive vs. an actual abnormality. In other words, each output C1 . . . CN may be seen as a confidence score indicating whether the candidate abnormality CA is an actual abnormality. In addition or as an alternative, trained function TF may be trained and configured such that it outputs further diagnostic information with respect to the candidate abnormality CA such as a degree of malignancy, a state of the contour (e.g., either smooth or spiculated), a degree of calcification or fat deposition, or degree of solidity, or other pathologically relevant observable of the underlying candidate abnormality CA. According to an embodiment, Step S50 is performed predominately in processing system 20.

At step S60, the N outputs C1 . . . . CN are used to calculate an overall or ensemble classification EC for the underlying candidate abnormality CA. Various ways of doing so are conceivable. According to an implementation, non-linear or linear combinations of outputs C1 . . . . CN are used to calculate ensemble classification EC. This may include calculating the average from the individual outputs C1 . . . . CN. Further, a weighted average may be used where the individual weights reflect the relevance of the specific output C1 . . . . CN for the overall result EC. With that, it can be accounted for that some transformations result in representations R1 . . . . RN (views) more relevant for deciding whether a false positive is present than others. For the same reason, non-linear combinations may be used to emphasize certain particularly relevant outputs C1 . . . . CN over others. According to another implementation, a further trained function may be used for determining ensemble classification EC of the candidate abnormality CA based on the N outputs R1 . . . . RN, and, optionally, the underlying image processing steps. Supplemental to the N outputs C1 . . . . CN as such, this further trained function may be provided with an indication of the transformation/image processing steps performed for generating the N representations R1 . . . . RN underlying the respective outputs C1 . . . . CN in order to appropriately weigh the individual outputs C1 . . . . CN. The further trained function may be embodied as a part of trained function TF. According to an embodiment, Step S60 is performed predominately in processing system 20.

Optional step S70 is directed to generate one or more actionable results based on the ensemble classification EC for the candidate abnormalities CA as provided for by steps S30 to S60. Results in general may relate to a list of findings FL with all relevant abnormalities which require further attention of the user. Optionally, the findings list FL may include any additional diagnostic information derived in the process. Optionally, the findings list FL may be of the form of a structured report, e.g., formatted according to the DICOM SR standard. Further, results may be in the form of a visualization comprising a rendering of one or more representations of the medical image data set MID with the relevant abnormalities highlighted for the user, e.g., by introducing symbols or text and/or applying designated colors. The result of the rendering can be in the form of one or more assistance images AI indicating to the user where the abnormalities are and/or what additional diagnostic information has been derived. The rendering may be a two-dimensional rendering on the basis of an appropriate view of the medical image data set MID such as a cross-section or slice through the image volume. The view may be selected manually by the user, e.g., by scrolling through the medical image data set MID, or (semi-) automatically by the system. Further, known volumetric rendering techniques such as raytracing, ray-casting or the like may be employed. In this regard, the user may specify parameters such as the viewing angle or the viewing distance. Preferably, this can be done in an interactive manner via user interface 10 with the help of a suited graphical user interface. Step S70 may comprise disregarding all candidate abnormalities CA the ensemble classification EC of which indicates that they relate to false positives and not to actual abnormalities. Disregarding in this respect may mean not taking false positives into account when generating a list of findings FL or deleting them from an already existing list of findings FL. Further, disregarding may mean not including false positives in assistance image AI. According to an implementation, a candidate abnormality CA may be regarded as false positive if its ensemble classification EC (e.g. in the form of an average confidence score) is below or above a predetermined threshold. According to an embodiment, Step S70 is performed predominately in processing system 20.

In optional step S80, the one or more results of the processing of steps S10-S70 is forwarded to the medical image system 40 for archiving the results for later use alongside with the medical image data sets MID. According to an implementation the results may be converted into one or more DICOM SR objects for appropriately forwarding and archiving. Preferably, step S80 is implemented such that the user has to actively decide whether or not she or he wants the evaluation results to be archived. This can be realized by a corresponding button in the graphical user interface running in user interface 10, for instance. Step S80 may be performed at least partially either on user interface 10 or on processing system 20. Corresponding data exchange is included in this step where necessary.

Trained function TF generally relates to an intelligent agent or classifier suited for classifying image data according to a learned task. It may relate to any type of method or apparatus capable of predicting to what group or category an object (in this case: the candidate abnormality CA in its respective representation R1 . . . RN) belongs. This definition comprises, but is not limited to, data mining tools and techniques such as Support Vector Machines, decision trees, naive Bayes or (convolutional) neural networks. Specifically, according to an implementation, the trained function may comprise a convolutional neural network. In an embodiment, the arrangement of the trained function is a fully convolutional network. Alternative network arrangements may be used, for example, a 3D Very Deep Convolutional Networks (3D-VGGNet). A VGGNet stacks many layer blocks containing narrow convolutional layers followed by max pooling layers. A convolutional neural network is defined in the form of a plurality of sequential layers. The term sequential is used to indicate the general flow of output feature values from one layer to input to a next layer. The information from the next layer is fed to a next layer, and so on until the final output layer. Layers may only feed forward or may be bi-directional, including some feedback to a previous layer. The layers may be weighted. Further, each layer generally comprises a number of nodes that are also weighted. Essentially, each node can be seen as executing a mathematical operation mapping one or more input values to an output value. The nodes of each layer may connect with all or only a sub-set of nodes of a previous and/or subsequent layer. Two nodes are "connected" if their inputs and/or outputs are connected. Input values for the nodes of the input layer are image element values, preferably pixel or voxel values, of the representations R1 . . . RN. The last layer is the output layer outputting outputs C1 . . . CN. In between input and output layer, there is a number of hidden layers. Various layers may be used, such as convolutional, pooling (e.g., max-pooling or average-pooling), up-sampling, deconvolutional, fully connected, or other types of layers. Convolutional layers convolve the input and pass its result to the next layer by moving an image filter kernel over the input. Pooling layers reduce the dimensions of the data by combining the outputs of node clusters at one layer into a single node in the next layer, thereby streamlining the underlying computation. Up-sampling and deconvolution layers reverse the actions of convolution and pooling layer in terms of the abstraction level. A fully connected layer connects every node in one layer to every node in another layer, so that essentially every feature gets a "vote". According to an implementation, skip connections may be used, so that layers may also output to other layers than the sequentially next layer introducing one or more residual blocks or layers. Such configuration is also referred to as ResNet. Using residual blocks results in the ability to train much deeper networks as this alleviates the vanishing gradient problem known from very deep neural networks.

The trained function of this embodiment learns by adapting weights or weighting parameters of individual layers and nodes based on training data. Rather than pre-programming potential signs of false positives and/or actual abnormalities and trying to identify these in the representations R1 . . . RN, trained function TF architecture is defined to learn these patterns at different levels of abstraction based on input data. Trained function TF may preferably be trained using a method according to supervised learning. Well established is the backpropagation method, which may be applied for embodiments of the present invention. During training, trained function TF is applied to training input values to produce corresponding output values the target values of which are known. The difference between produced and target output values (e.g., in the form of the mean squared error (MSE) of the difference between produced and target values) may be used to introduce a cost or loss function as a measure of how good or bad trained function TF performs. The goal of the training is to find a (local) minimum of the loss function by iteratively adjusting the weights of trained function TF so that trained function is finally enabled to generate acceptable results across a (sufficiently) large cohort of training data. This optimization problem can be carried out using stochastic gradient descent or other approaches known in the art.

Figure 4:
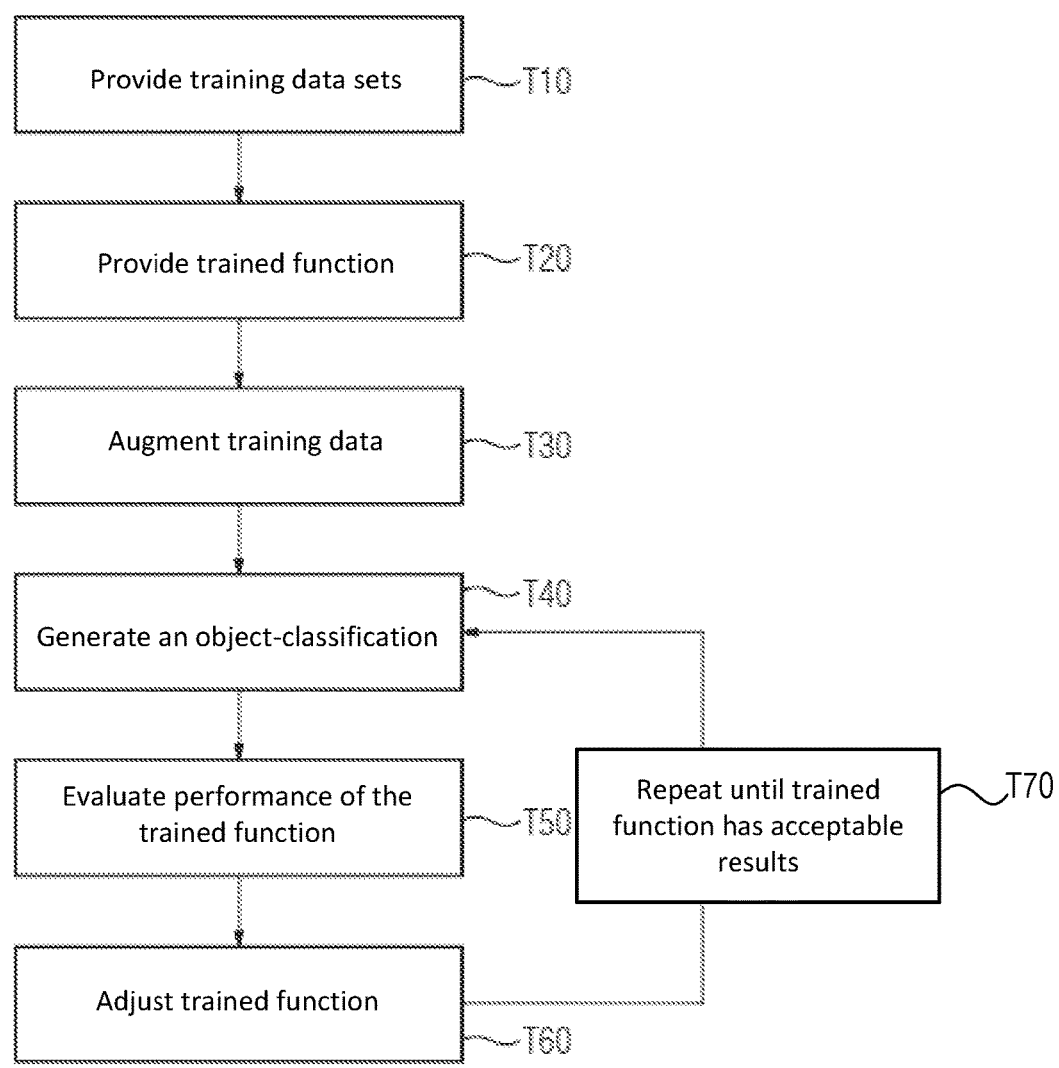
FIG. 4 depicts a flowchart illustrating a method for training trained functions to detect one or more anatomic landmarks in medical image data according to an embodiment.

FIG. 4 depicts an inventive method of an embodiment for training trained function TF to classify a candidate abnormality CA identified in a medical image data set MID. It is an idea of the proposed training method to also leverage the proposed data augmentation as described in connection with FIGS. 2 and 3. Rather than generating different representations of a candidate abnormalities CA to improve the basis for deriving a classification, the data augmentation is now used to increase the amount of available training data. The order of the steps does not necessarily correspond to the numbering of the steps but may also vary between different embodiments of the present invention.

A first step T10 is directed to provide one or more training data sets. The training data sets each comprise training image data. The training image data respectively relates to an image volume containing an object (e.g., in the form of an image pattern) the classification of which shall be determined by the trained function. Further, the training data sets each comprise a target classification of the respective object. The target classification is preferably provided in the form of the expected output of the trained function. As discussed in connection with step S30, this may be in the form of a binary output (actual abnormality or false positive), a confidence score, or additional diagnostic information (degree of malignancy etc.). Further, the training image data may comprise an indication of the object, e.g., in the form of its center coordinates and size, as discussed in connection with step S20. According to an implementation, the target classification is based on an annotation by a human. The objects comprised in the training data sets may thus also designated as annotated objects. The training image data is preferably of the same type as the original image data to be processed by the deployed and readily trained system. Accordingly, the training image data each likewise relate to an imaging volume from a body part of a patient acquired using one of the abovementioned medical imaging modalities.

Step T20 is directed to provide a trained function which shall be trained or further trained. Providing may mean fetching an appropriate function from an archive and/or loading it into a memory.

At subsequent step T30, the available training data is augmented. This is done by generating, for each of the available annotated objects, a plurality of representations. Thereby, the same methodology as discussed in connection with step S30 may be applied. As explained in connection with step S30, the number of representations for each object may be the same for each object or dynamically set for each object. For each of the representations, the target classification of the underlying object is retained and associated. At the end of step T30, the training data has been enhanced in that the number of representations which may be used for training is multiplexed. Assuming that N representations per object are generated for M objects, N times M representations result. Not only this is beneficial in that the training data is augmented, but the trained function is also provided with multiple different views per object very much like it will be the case during deployment.

At subsequent step T40, an object-classification is generated by applying the trained function TF to one of the representations. As explained in connection with step S40, the classification may generally be in the form of an output C1 . . . CN.

The performance of the trained function TF (i.e., the quality of the classification) is evaluated in subsequent step T50. To this end, the classification generated in step T40 is compared to the corresponding target classification.

The comparison may then be used as a basis for calculating a loss function to adjust the trained function TF at step T60. At step T70, the steps of generating classifications by the trained function TF (step T40), comparing the result to the known output (step T50), and adjusting the trained function TF (step T60) are repeated with paired sets of representations and target classifications until the trained function is able to generate results that are acceptable (i.e., until a local minimum of the loss function is reached). Once all pairs have been used, pairs are randomly shuffled for the next pass.

Figure 5:
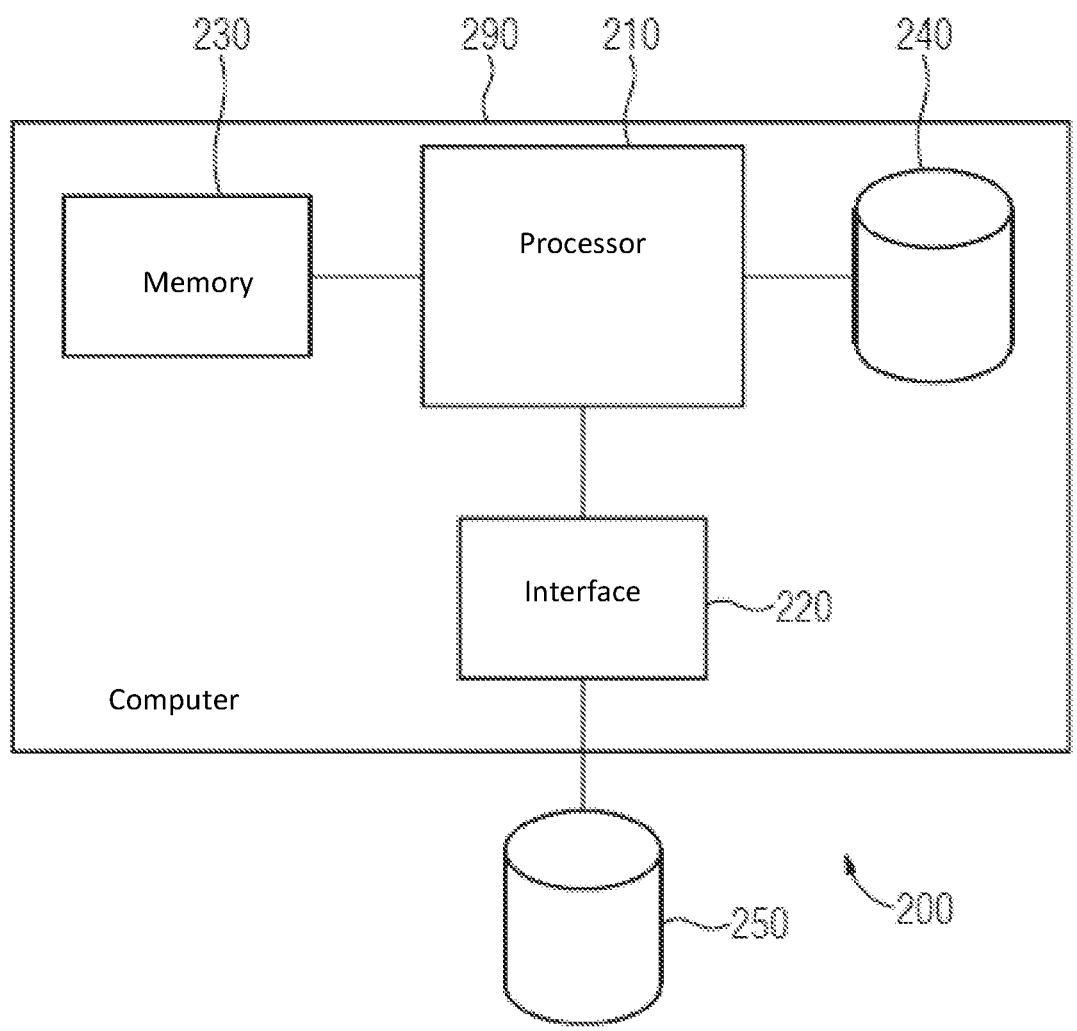
FIG. 5 shows a system for training trained functions to detect one or more anatomic landmarks in medical image data according to an embodiment.

FIG. 5 illustrates an embodiment of a system 200 for training trained function TF. The system comprises a processor 210, an interface 220, a memory 230, a storage 240, and a database 250. Processor 210, interface 220, memory 230 and storage 240 may be embodied by a computer 290. Processor 210 controls the overall operation of the computer 290 by executing computer program instructions which define such operation. The computer program instructions may be stored in memory 230 or in storage 240 and loaded into memory 230 when execution of the computer program instructions is desired. Storage 240 may be a local storage as a component of the system 200, or a remote storage accessible over a network, such as a component of a server or cloud system. The method steps illustrated in FIG. 4 may be defined by the computer program instructions stored in memory 230 and/or storage 240, and controlled by processor 210 executing the computer program instructions.

Database 250 is a storage device such a cloud or local storage serving as an archive for the training data sets and/or the training representations. Database 250 may be connected to computer 290 for receipt of one or more training representations by the computer 290. It is also possible to implement database 250 and computer 290 as a single device. It is further possible that database 250 and computer 290 communicate wirelessly or with wired connection through a network. Interface 220 is configured to interact with database 250.

Wherever meaningful, individual embodiments or their individual aspects and features can be combined or exchanged with one another without limiting or widening the scope of the present invention. Advantages which are described with respect to one embodiment of the present invention are, wherever applicable, also advantageous to other embodiments of the present invention.

The following points are also part of the disclosure:

1. Computer-implemented method for classifying an object identified in an image data set comprising original image data, the method comprising the following steps:
    generating a plurality of different representations of the object, each of the plurality of different representations comprising processed image data generated by applying one or more image processing steps to the original image data comprised in at least a region of interest containing the object;
    providing a trained function, the trained function being trained to generate an output based on an individual representation of the object, the output comprising an indication of a classification of the object in view of the individual representation;
    applying the trained function to each representation of the plurality of representations so as to generate a corresponding plurality of outputs, each of the plurality of outputs corresponding to one representation of the plurality of different representations;
    determining an ensemble classification of the object based on the plurality of outputs.
2. Method according to 1, wherein applying one or more image processing steps comprises applying one or more mathematical transformations, optionally, affine and/or non-affine transformations.
3. Method according to 2, wherein the mathematical transformations are selected from the group including
    one or more rotation transformations configured to generate processed image data rotated with respect to the original image data by an angle of rotation around an axis of rotation;
    one or more mirror transformations configured to generate processed image data mathematically reflected with respect to the original image data by a mirror plane;
    one or more scaling transformations configured to generate up- or down-scaled processed image data;
    one or more shear transformations configured to generate sheared processed image data, and
    any combination of the afore-mentioned.
4. Method according to any of the preceding points, wherein applying one or more image processing steps comprises applying one or more image filters.
5. Method according to 4, wherein the image filters are selected from the group including:
    one or more smoothing filters,
    one or more contrast enhancement filters,
    one or more color filters,
    one or more distortion filters,
    one or more blur filters,
    one or more high- or low-pass filters,
    one or more convolution filters,
    one or more deconvolution filters,
    any combination of the afore-mentioned.
6. Method according to any of the preceding points, wherein applying one or more image processing steps comprises applying one or more different cropping frames.
7. Method according to 6, wherein applying one or more different cropping frames comprises using different relative positions of the cropping frames with respect to the object.
8. Method according to any of the preceding points, wherein
    the trained function is configured such that the output corresponds to a classification score, and
    the step of determining an ensemble classification is based on calculating a linear and/or non-linear combination of the plurality of classification scores respectively corresponding to the plurality of outputs, optionally, in the form of a weighted sum of the plurality of classification scores or an average over the plurality of classification scores.
9. Method according to 8, wherein
    the image data set is a medical image data set depicting a body part of a patient; and
    the step of determining a classification involves classifying the object as false positive if the linear and/or non-linear combination of the plurality of classification scores is lower than a predetermined threshold and as a pathological abnormality if the linear and/or non-linear combination of the plurality of classification scores is higher than a predetermined threshold.
10. Method according to any of the preceding points, wherein
    the image data set is a medical image data set depicting a body part of a patient; and
    the step of determining an ensemble classification involves generating a result indicative of the pathological relevance of the object, in particular, whether or not the abnormality is malignant of benign.
11. Method according to any of the preceding points, wherein
    in the step of generating plurality of different representations,
    the image processing steps comprise rotations of the volume of interest at M angles and reflections in K dimensions.
12. Method according to any of the preceding points, wherein
    in the step of generating the plurality of different representations,
    the image processing steps at least comprise: a rotation of the region of interest by 90° with respect to an axis of rotation, a rotation of the region of interest by 180° degrees with respect to the axis of rotation, and a rotation of the region of interest by 270° with respect to the axis of rotation, the axis of rotation preferably being one of the main axes spanned by the medical image data set.
13. Computer-implemented method for training a trained function for classifying objects in computer aided diagnosis of medical image data sets depicting a body part of a patient, the method including the following steps:
    providing a training data set, wherein the training data set includes: training image data relating to an image volume containing an object to be classified; and target a classification of the object;

generating N>1 different representations of the object, each of the N different representations comprising processed image data generated by applying one or more image processing steps to the training image data;

generating a classification of the object by applying the trained function to one of the representation;

comparing the classification with the target classification; and adjusting the trained function as a function of the comparison.

14. Computer-implemented method for classifying a region of interest in an image data set, the method including the following steps:

generating a plurality of different representations of the region of interest;

determining, for each of the representations, a classification to generate a corresponding plurality of classifications;

calculating an ensemble classification for the region of interest based on the plurality of classifications.

Finally, it should again be noted that the devices and methods described above in detail are merely example embodiments which can be modified by a person skilled in the art in a wide variety of ways without departing from the scope of the invention. Furthermore, the use of the indefinite article "a" or "an" does not preclude the possibility that the relevant features can also be present plurally. Similarly, the expression "unit" does not preclude this including a plurality of components which can possibly also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for classifying a region of interest in a medical image data set depicting a body part of a patient, the region of interest including an object of potential pathological relevance, the computer-implemented method comprising:

obtaining a medical image data set of the region of interest;

generating a plurality of different representations of the region of interest from the medical image data set by applying one or more different image processing steps to the medical image data set, the one or more different image processing steps including one or more of mathematical transformations, image smoothing, image sharpening, contrast enhancement, edge enhancement, color filtering, de-noising, blurring, de-blurring histogram equalization, high-pass filtering, low-pass filtering, convolution filtering, or deconvolution filtering;

determining a classification for each of the plurality of different representations to generate a plurality of classifications, each classification indicating a pathological relevance of the object in a corresponding representation; and calculating an ensemble classification for the region of interest based on the plurality of classifications.

2. The computer-implemented method of claim 1, wherein the mathematical transformations include affine and non-affine transformations.

3. The computer-implemented method of claim 1, wherein the one or more different image processing steps further include at least one of:

rotating the region of interest, mirroring the region of interest, scaling the region of interest, shearing the region of interest, or translating the region of interest in image space of the medical image data set.

4. The computer-implemented method of claim 1, wherein the determining includes using a trained function to generate the classification for each of the plurality of different representations.

5. The computer-implemented method of claim 4, wherein the trained function is based on at least one of Support Vector Machine, naive Bayes, neural network, decision tree, or Res-Net.

6. The computer-implemented method of claim 1, wherein the calculating the ensemble classification is based on calculating at least one of a linear or non-linear combination of the plurality of classifications.

7. The computer-implemented method of claim 1, wherein each classification includes an indication of whether the object relates to a pathological relevant abnormality or to a false positive.

8. The computer-implemented method of claim 1, further comprising:

identifying the region of interest automatically or manually by a user.

9. A computer-implemented method for detecting pathologically relevant abnormalities in a medical image data set depicting a body part of a patient, the computer-implemented method comprising:

receiving a medical image data set;

determining a set of candidate abnormalities in the medical image data set;

for each candidate abnormality in the set of candidate abnormalities generating a plurality of different representations of the candidate abnormality from the medical image data set by applying one or more different image processing steps to the medical image data set, the one or more different image processing steps including one or more of mathematical transformations, image smoothing, image sharpening, contrast enhancement, edge enhancement, color filtering, de-noising, blurring, de-blurring histogram equalization, high-pass filtering, low-pass filtering, convolution filtering, or deconvolution filtering, determining a plurality of classifications, each classification of the plurality of classifications corresponding to one of the plurality of different representations, and each classification being indicative of a pathological relevance of the candidate abnormality in a corresponding representation, and determining an ensemble classification of the candidate abnormality based on the plurality of classifications; and generating a detection result using the ensemble classifications of each of the candidate abnormalities.

10. The computer-implemented method of claim 9, wherein the generating of the detection result comprises:

eliminating one or more of the candidate abnormalities from the set of candidate abnormalities based upon a corresponding ensemble classification.

11. A system for detecting pathologically relevant abnormalities in a medical image data set depicting a body part of a patient, the system comprising:

an interface unit configured to receive a medical image data set; and a processor configured to cause the system to determine a set of candidate abnormalities in the medical image data set, for each candidate abnormality in the set of candidate abnormalities generate a plurality of different representations of the candidate abnormality from the medical image data set by applying one or more different image processing steps to the medical image data set, the one or more different image processing steps including one or more of mathematical transformations, image smoothing, image sharpening, contrast enhancement, edge enhancement, color filtering, de-noising, blurring, de-blurring histogram equalization, high-pass filtering, low-pass filtering, convolution filtering, or deconvolution filtering, determine a plurality of classifications, each classification of the plurality of classifications corresponding to one of the plurality of different representations, and determine an ensemble classification of the candidate abnormality based on the plurality of classifications, and generate a detection result using the ensemble classifications of each of the candidate abnormalities.

12. A non-transitory computer program product storing program elements, which induce a computing unit of a system to perform the method of claim 1 when the program elements are loaded into a memory of the computing unit and executed.

13. A non-transitory computer-readable medium storing program elements, readable and executable by a computing unit of a system to perform the method of claim 1 when the program elements are executed by the computing unit.

14. The computer-implemented method of claim 6, wherein the calculating the ensemble classification is based on calculating at least one of a linear or non-linear combination of the plurality of classifications in a form of a weighted sum of the plurality of classifications or an average of the plurality of classifications.

15. The computer-implemented method of claim 1, wherein the one or more different image processing steps further include performing a combination of rotations of the region of interest and reflections of the region of interest to generate a plurality of viewing directions of the region of interest.

* * * * *